United States Patent [19]

Peattie et al.

[11] Patent Number: 5,763,590
[45] Date of Patent: Jun. 9, 1998

[54] ISOLATION OF AN $M_R$ 52,000 FK506 BINDING PROTEIN AND MOLECULAR CLONING OF A CORRESPONDING HUMAN CDNA

[75] Inventors: Debra A. Peattie, Cambridge; Matthew W. Harding, Acton; David J. Livingston, Newtonville, all of Mass.

[73] Assignee: Vertex Pharmaceuticals, Inc., Cambridge, Mass.

[21] Appl. No.: 336,618

[22] Filed: Nov. 9, 1994

Related U.S. Application Data

[63] Continuation of Ser. No. 218,989, Mar. 29, 1994, abandoned, which is a continuation of Ser. No. 963,325, Oct. 16, 1992, abandoned, which is a continuation-in-part of Ser. No. 777,752, Oct. 11, 1991, abandoned.

[51] Int. Cl.$^6$ .................................................. C12N 15/12
[52] U.S. Cl. ........................ 536/23.5; 536/23.2; 435/233; 530/350
[58] Field of Search ........................... 435/233; 530/350; 536/23.2, 23.5

[56] References Cited

FOREIGN PATENT DOCUMENTS

| 0 379 342 | 1/1990 | European Pat. Off. . |
| 0 372 862 | 6/1990 | European Pat. Off. . |
| WO 91/17439 | 11/1991 | WIPO . |
| WO 93/07269 | 4/1993 | WIPO . |

OTHER PUBLICATIONS

Harding, M.W., et al., "Isolation and Amino Acid Sequence of Cyclophilin", Jour. of Biol. Chem., 261(18), pp. 8547–8555 (1986).
Sawada, S., et al., "Novel Immunosuppressive Agent, FK506 In Vitro Effects on the Cloned T Cell Activation", Jour. of Immun., 139(6), pp. 1797–1803 (1987).
Warty, V., et al., "FK506: A Novel Immunosuppressive Agent Characteristics of Binding and Uptake by Human Lymphocytes", Transpl., 46, pp. 453–455 (1988).
Siekierka, J.J., et al., "A cytosolic binding protein for the immunosuppressant FK506 has peptidyl-prolyl isomerase activity but is distinct from cyclophilin", Nature, 341, pp. 755–757 (1989).
Harding, M.W., et al., "A receptor for the immunosuppressant FK506 is a cis-trans peptidyl–prolyl isomerase", Nature, 341, pp. 758–760 (1989).
Dumont, F.J., et al., "The immunosuppressive macrolides FK–506 and Rapamycin act as reciprocal antagonists in murine T cells", J. of Immun., 144(4), pp. 1418–1424 (1990).
Siekierka, J.J., et al., "The cytosolic-binding protein for the immunosuppressant FK–506 is both a Ubiquitos and Highly Conserved Peptidyl–Prolyl Cis–Trans Isomerase", J. of Biol. Chem., 265(34), pp. 21011–21015 (1990).
Harrison, R.K., et al., "Substrate Specificities of the Peptidyl Prolyl Cis–Trans Isomerase Activities . . . Family of Distinct Enzymes", Biochem., 29(16), pp. 3813–3816 (1990).
Standaert, R.F., et al., "Molecular cloning and overexpression of the human FK506–binding protein FKBP", Nature, 346, pp. 671–674 (1990).

Schreiber, S.L., "Chemistry and Biology of the Immunophilins and their Immunosuppressive Ligands", Science, 251, pp. 283–287 (1991).
Fretz, H., et al., "Rapamycin and FK506 Binding Proteins (Immunophilins)", J. Am. Chem. Soc., 113, pp. 1409–1411 (1991).
Michnick, S.W., et al., "Solution Structure of FKBP, a Rotamase Enzyme and Receptor for FK506 and Rapamycin", Science, 252, pp. 836–839 (1991).
Van Duyne, G.D., et al., "Atomic Structure of FKBP–FK506, an Immunophilin–Immunosuppressant Complex", Science, 252, pp. 839–842 (1991).
Moore, J.M., et al., "Solution structure of the major binding protein for the immunosuppressant FK506", Nature, 351, pp. 248–250 (1991).
Liu, J., et al., "Calcineurin is a common target of cyclophilin–Cyclosporin A and FKBP–FP506 Complexes", Cell, pp. 807–815 (1991).
Jin, Y–J., et al., "Molecular cloning of a membrane–associated human FK506–and Rapamycin–binding protein, FKBP–13", Proc. Natl. Acad. Sci. USA, 88, pp. 6677–6681 (1991).
Rosborough, S.L., et al., "Identification of FKBP–Related Proteins with Antibodies of Predetermined Specificity and Isolation by FK506 Affinity Chromatography", Trans. Proc., 23(6), pp. 2890–2893 (1991).
Palaszynski et al., "Purification and Characterization of Cyclosporine and FK–506 Binding Proteins From A Human T–Helper Cell Line," Clin Biochem, 24, pp. 63–70 (1991).
Donnelly et al., "Cyclosprine, FK–506, and Rapamycin Interactions With A Cytosolic Binding Protein," FASEB J., 5, Abs. 2092 (1991).
Donnelly et al., "Purification of a 50– to 58kDa Immunophilin from Human Spleen and a Jurkat T–Cell Line Capable of Binding Cyclosporine A, FK 506, and Rapamycin," Transplant Proc., 23, pp. 2886–2889 (1991).
Donnelly et al., "Cyclosporine and FK 506 May Share A Common Cytosolic Binding Protein," Clin. Chem., 36(6), Abs. 0384 (1990).
Donnelly et al., "Cyclosporin G and Metabolite Binding to Cyclophilin and a 50 kDa Binding Protein Related to In Vitro Immunosuppression", Clin. Biochem, 39, pp. 122–125 (1993).
Donnelly, J.G., "Purification and Characterization of a 50 kDa Lymphocyte–Derived Binding Protein for Cyclosporin, FK 506 and Rapamycin", Doctoral Thesis, George Washington University, pp. 182–183, 190 (1993).
Sanchez et al., Biochemistry, vol. 29:5145–5152, 1990.
Lathe, R., J. Mol. Biol., vol. 183:1–12, 1985.
Sambrook et al., Molecular Cloning: A Laboratory Manual, Cold Spring Harbor Press, pp. 11.3–11.19, 1989.

Primary Examiner—Keith D. Hendricks
Attorney, Agent, or Firm—Fish & Neave; James F. Haley, Jr.; Margaret A. Pierri

[57] ABSTRACT

An FK506 binding protein of mammalian origin of approximate size $(M_r)$ 52,000, isolated by FK506 affinity chromatography and a corresponding human cDNA of approximate size 2.2 Kb, isolated by screening a human placenta cDNA library with a DNA probe whose sequence predicts a consensus amino acid sequence present in five FKBP12 sequences and in the human FKBP13 sequence.

2 Claims, 4 Drawing Sheets

FIG. 1

N-terminal sequence

H$_2$-N-Thr-Ala-Glu-Glu-Thr-Lys-Ala-Ala-Glu-Ser-Gly-Ala-Gln-Ser-Ala-Pro-Leu-Arg-Leu-Glu-Gly-Val-Asp-Ile-Ser-Pro-Lys$_{27}$

1. Asp-Arg-Phe-Ser-Phe-Asp-Leu-Gly-Lys
2. Ala-xxx-Asp-Ile-Ala-Val-Ala-Thr
3. Met-Lys-Val-Gly-Glu-Val-xxx-His-Ile-Thr-Cys-Lys
4. Ile-Pro-Pro-Asn-Ala-Thr-Leu-Val-Phe-Glu-Val-Glu-Leu-Phe-Glu-Phe-Lys
5. Pro-Asn-Glu-Gly-Ala-Leu-Val-Glu-Val-Ala-Leu-Glu-xxx-Tyr-Phe-Gln
6. Tyr-Glu-Ile-His-Leu-Lys
7. Gly-Thr-Val-Tyr-Phe-Lys
8. Ala-Leu-Glu-Leu-Asp-Ser-Asn-Asn-Glu-Lys
9. Leu-Tyr-Ala-Asn-Met-Phe-Glu-Leu-Ala-Ala-Glu-Glu-Glu-xxx-Lys
10. Ala-Leu-Val-Ala-Ala-Gly-Asp-Gln-Pro-Ala-Asp-Ala-Glu-Met-Arg-Asp-Glu-Pro Internal sequence of peptides (xxx=indeterminate amino acid)

FIG.2a

```
Consensus    M                                                  G  G  P  G     VHYTG   L  DG KFD  SS  DR       F  F  L  GK EVI   W
hFKBP52      M TAEEMKATES GAQSAPLPME GVDISPKQDE GVL--KVIKREG TGTEMPMIGD RVFVHYTGW-L LDGTKFD------SSL DR-K-DKFSFDL GKGEVIKAWD91
bFKBP52        TAEETKAAES GAQSAPLRLE GVDISPK                                                  DRFSFDL  GK     A*D
hFKBP12                                          GVQ--VETISPG TGTEMPMIGD RVFVHYTGM-L EDGKKFD------SSR DR-N-KPFKFML GKQEVIRGWE60
bFKBP12                                        M GVQ--VETISPG DGRTFPKRGQ TCVVHYTGM-L EDGKKFD------SSR DR-N-KPFKFTL GKQEVIRGWE
mFKBP12                                          GVQ--VETISPG DGRTFPKRGQ TCVVHYTGM-L EDGKKFD------SSR DR-N-KPFKFVL GKGEVIRGWE
bFKBP12                                          ------IDRISPG DGRTFPKTGD DGATFPKTGD LVTIHYTGT-L ENGQKFD------SSV DR-G-SPFQCNI GVGQVIKGWD
ScFKBP12       M SEVIEGNVK-   GLQ--IEVQQEG QGTRETRRGD NVDVHYKGV-L TSGKKFD------ASY DR-G-EPLNFTV GQGQVIKGWD
NcFKBP12       M TIPQLD----   TATGAEGKRR LQIGVKKR--VD HCPIKSRKGD VLHMHYTGK-L EDGTEFD------SSL PQ-N-QPFVFSL GTGQVIKGWD
hFKBP13      MRLSWFRVLT VLSICLSAVA TGTEGKRK       LQIGVKKR--VD HCPIKSRKGD VLHMHYTGK-L EDGTEFD------SSL PQ-N-QPFVFSL GTGQVIK
bFKBP13                        TGTEGKRK          LEIGIIKRIPVE DCLIKAMPGD KVKVHYTGSLL ESGTVFD------SSY SR-G-SPIAFEL GVGRVIKGWD
ScFKBP13     MMFNIYLFVT FFSTIL----- ---AGSLSD      KYT--KSVLKG DKTNFPKKGD VHCWYTGT-L QDCTVFDTNIQTSAK KKKNAKPLSFKV GVGKVIRGWD
hFKBP25      KVSEQVKNVK LNEDKPKETK SEETLDEGPP 
X17068         ARGGG ERGAVGVPLE GVDISPKQDE GVL--KVIKREG TGTETPMIGD RVFVHYTGW-L LDGTKFD------SSL DR-K-DKFSFDL GVGKVIKAWD
X17069         ARGGG ERGAVGVPLE GVDISPKQDE GVL--KVIKREG TGTETPMIGD RVFVHYTGW-L LDGTKFD------SSL DR-K-DKFSFDL GKGEVIKAWD
p59          M TAEEMKAAES GAQSAPLPLE GVDISPKQDE GVL--KVIKREG TGTETPMIGD RVFVHYTGW-L LDGTKFD------SSL DR-K-DKFSFDL GKGEVIKAWD Consensus     A  M VG     T  P Y AYG  G  P          IPP  ATLVF   VEL
hFKBP52      IAIATMKVGE VCHITCKPEY AYGSAGSPP-K IPPNATLVFE VELFEFKGED LTEEEDGGII RIQTRGEGY AKPNEGAIVE VALEGYYKDK LFDQRELRFE
bFKBP52      IAVATMK                                                            PNEGALVE VALE
hFKBP12      EGVAQMSVGQ RAKLTISPDY AYGATGHPG-I IPPHATLVFD VELFEF
mFKBP12      EGVAQMSVGQ RAKLIISSDY AYGATGHPG-I IPPHATLVFD VELLKLE107
bFKBP12      EGVAQMSVGQ RAKLTISPDY AYGATGHPG-I IPPNATLIFD VELLKLE
bFKBP12      VGIPKLSVGE KARLTIPGPY AYGPRGFPG-L IPPNSTLVFD VELLKVN
ScFKBP12     EGLLGMKIGE KRKLTIAPHL AYGNRAVGG-I IPANSTLIFE TELVGIKGVQ KGE
NcFKBP12     QGLLGMCEGE KRKLVIPSEL GYGERGAPP-K IPGGATLVFE VELLKIERRT EL
bFKBP13        EGE KRKLVIPSEL GYGERGAPP-K 
ScFKBP13     QCVAGMCVGE KRKLQIPSSL AYGERGVPG-V IPPSADLVFD VELVDVKSAA
hFKBP25      EALLTMSKGE KARLEIEPEW AYGKKGQPDAK            VELVDID
X17068       IAVATMKVGE VCHITCKPEY AYGAAGSPP-K IPPNATLVFE VELFEFKGED LTEEEDGGII RRIRLGVKAM QGPNDGAMVE VALEGYHKDR LFDQRELCFE
X17069       IAVATMKVGE VCHITCKPEY AYGAAGSPP-K IPPNATLVFE VELFEFKGED LTEEEDGGII RRIRLGVKAM QGPNDGAMVE VALEGYHKDR LFDQRELCFE
p59          IAVATMKVGE LCRITCKPEY AYGSAGSPP-K IPPNATLVFE VELFEFKGED LTDDEDGGII RRIRTRGEGY ARPNDGAIVE VALEGYYKDR LFDQRELRFE
```

```
hFKBP52    IGEGENLDLP YGLERAIQRM EKGEHSIVYL KPSYAFGSVG KEKFQIPPNA ELKYELHLKS FEKAKESWEM NSEEKLEQST IVKERGTVYF KEGKYKQALL291
bFKBP52                                     GEHSIVYL K                      YEIHLK                                GTVYF K
X17068     VGEGESLDLP CAWRRPFSAW RKESIPSCTS NLAMLLAVWG RRGSRSHRTA ELRYEVRLKS FEKAKESWEM SSARSWSRAT YVKERGTAYF KEGKYKQALL
X17069     VGEGESLDLP CAWRRPFSAW RKESIPSCTS NLAMLLAVWG RRGSRSHRTA ELRYEVRLKS FEKAKESWEM SSARSWSRAT YVKERGTAYF KEGKYKQALL
p59        VGEGESLDLP CGLEKAIQRM EKGEHSILYL KPSYAFGNAG KEKFQIPPYA ELKYEVHLKS FEKAKESWEM SSEEKLEQSA IVKERGTVYF KEGKYKQALL hFKBP52    QYKKIVSWLE YESSFSNEEA QKAQALRLAS HLNLAMCHLK LQAFSAAIES CNKALELDSN NEKGLFRRGE AHLAVNDFEL ARADFQKVLQ LYPNNKAAKT391
bFKBP52                                                           ALELDSN    NEK
X17068     QYKKIVSWLE YESSFSGEEM QKVHALRLAS HLNLAMCHLK LQAFSAAIES CNKALELDSN NEKGLFRRGE AHLAVNDFDL ARADFQKVLQ LYPSNKAAKT
X17069     QYKKIVSWLE YESSFSGEEM QKVHALRLAS HLNLAMCHLK LQAFSAAIES CNKALELDSN NEKGLFRRGE AHLAVNDFDL ARADFQKVLQ LYPSNKAAKT
p59        QYKKIVSWLE YESSFSSEEV QKAQALRLAS HLNLAMCHLK LQAFSAAVES CNKALELDSN NEKGLFRRGE AHLAVNDFDL ARADFQKVLQ LYPSNKAAKA hFKBP52    QLAVCQQRIR RQLAREKKLY ANMFERLAEE ENKAKAEASSG DHPTDTEMK EEQKSNTAGS QSQVETEA459
bFKBP52                       LY ANMFERLAEE ETK  ALVAAG DQPADAEM
X17068     QLAVCQQRTR RQLAREKKLY ANMFERLAEE EHKVKAEVAAG DHPTDAERK SLPRVWPPMD TKMQSLPTTH PHPHSSSRPQ SHTSNQCNQC TCSHHCRSCS
X17069     QLAVCQQRTR RQLAREKKLY ANMFERLAEE EHKVKAEVAAG DHPTDAEMK GERN-NVAEN QSRVETEA
p59        QLAVCQQRIR KQIAREKKLY ANMFERLAEE ENKAKAEVAAG DHPMDTEMK DERN-DVAGS QSQVETEA

X17068     QAGHAGSSSS PSPGPPMKHP KPSVHSRHSP ARPSHRGSCPK NRKTFEGKV SKRKAVRRRK RTHRAKRRSS GRRYK
```

ISOLATION OF AN $M_R$ 52,000 FK506 BINDING PROTEIN AND MOLECULAR CLONING OF A CORRESPONDING HUMAN CDNA

RELATED APPLICATION

This is a continuation of application Ser. No. 08/218,989, filed Mar. 29, 1994, now abandoned entitled ISOLATION OF AN $M_r$52,000 FK506 BINDING PROTEIN AND MOLECULAR CLONING OF A CORRESPONDING HUMAN cDNA, which is a continuation of application Ser. No. 07/963,325, filed Oct. 16, 1992, now abandoned, which is a continuation-in-part of Ser. No. 07/777,752, filed Oct. 11, 1991, now abandoned, the teachings of which are herein incorporated by reference.

GOVERNMENT FUNDING

The invention described herein was supported in whole or in part by Grant No. AI29804 from the National Institutes of Health.

BACKGROUND OF THE INVENTION

FK506 and rapamycin are structurally related macrolides that block distinct steps in intracellular signalling pathways. (Sawada, S. et al., *J. Immunol.*, 139:1797–1803 (1987); Tocci, M. J., et al., *J. Immunol.*, 143:618–726/(1989)). Both are potent immunosuppressants, and drug action is mediated in part by binding to members of the immunophilin protein family. (Schreiber, S. L., *Science*, 251:283–287 (1991); Rosen, M. K. and Schrieber, S. L., *Angew. Chem. Int. Ed. Engl.*, 31:384–400 (1992)). One recently identified FK506 binding protein (FKBP) is FKBP12 with approximate relative molecular mass ($M_r$) of 11,800 (12K), and a PI of 8.8–8.9. (Harding, M. W., et al., *Nature*, 341:758–760 (1989)). Studies have shown that the unbound FKBP12 catalyzes the cis-trans isomerization of proline residues in proteins and peptides. However, when FKPB12 binds FK506, this activity is inhibited. Recent studies suggest that the FK506-FKBP12 complex functions as an immunosuppressant by binding to, and altering, the phosphatase activity of calcineurin/calmodulin.

SUMMARY OF THE INVENTION

The present invention relates to the isolation of an FK506 binding protein (FKBP) of mammalian origin of approximate size ($M_r$) 52,000 and to the molecular cloning of a corresponding human cDNA from a human placental cDNA library.

The $M_r$ 52,000 protein, hereinafter referred to as FKBP52, is a cytosolic protein isolated from bovine thymus by FK506 affinity chromatography and is a new member of a class of immunosuppressant FK506 binding proteins that play a key role in regulating immune responses. A partial amino acid sequence of FKBP52 (approximately 30% of the complete protein sequence) is presented herein. The remaining sequence can be subsequently determined using known methods, such as those used to determine the partial sequence.

The human cDNA clone which is the subject of the present invention was isolated by screening a human placental cDNA library with a DNA probe whose sequence predicted a consensus amino acid sequence present in five FKBP12 sequences (human, murine, bovine, *Saccharomyces cerevisiae* and *Neurospora crassa*), and in the human FKBP13 sequence, another recently identified FK506 binding protein. A clone identified in this manner contained a cDNA insert of approximately 2.2 kilobases.

The cDNA insert was purified and sequenced in its entirety. The nucleotide sequence of the coding strand (2167 bases), including the ATG initiation codon and the TAG stop codon for the deduced protein product (the correct open reading frame), is presented herein. The amino acid sequence of the protein product of the open reading frame of the human cDNA clone was deduced. The deduced protein has 459 amino acids and an $M_r$ of 51,810, which is essentially the same $M_r$ as that of FKBP52.

Thus, the present invention includes a $M_r$ 52,000 FK506 binding protein (FKBP52) of mammalian origin, particularly a bovine and human $M_r$ 52,000 protein, DNA or RNA encoding FKBP52, and nucleic acid probes which hybridize with DNA or RNA encoding FKBP52.

The present invention also includes FKBP52 homologues or equivalents (i.e., proteins which have amino acid sequences substantially similar, but not identical, to that of FKBP52 and exhibit FK506 binding characteristics). This invention further includes peptides (FKBP52 fragments which retain FK506 binding affinity, yet are less than the entire FKBP52 amino acid sequence), monoclonal and polyclonal antibodies specific for FKBP52, and uses for the nucleic acid sequences, FKBP52, FKBP52 equivalents, and FKBP52 specific antibodies. These uses include methods of screening for new immunosuppressive compounds, methods of measuring the parent compound and/or metabolites in biological samples obtained from individuals taking immunosuppressive drugs, methods of identifying natural intracellular rapamycin-like and FK506-like substances (i.e., molecules or compounds) which function in regulation of cellular metabolism, and methods of identifying natural intracellular substrates which are potential targets for other novel immunosuppressive agents.

Furthermore, as discussed herein, FKBP52 is associated with the 90 kDa heat shock protein (hsp90) in untransformed steroid receptor complexes. Therefore, FKBP52 may also be useful in mediating steroidal hormone receptor transformation.

BRIEF DESCRIPTION OF THE DRAWING

FIG. 1 is the partial amino acid sequence of the $M_r$ 52,000 protein (FKBP52). FIG. 1A is the N-terminal sequence of the bovine $M_r$ 52,000 FKBP52 (SEQ ID NO: 1). FIG. 1B is the internal sequence data determined after endoproteinase Lysine C cleavage (SEQ ID NOS: 2–11).

FIG. 2 depicts the deduced sequence of hFKBP52 (SEQ ID NO: 12) and 133 chemically determined residues of bFKBP52 (SEQ ID NOS: 2–11) and shows that they align well with other known FKBPs (SEQ ID NOS: 12–21), polypeptides encoded by the GenBank murine cDNAs X17068 (SEQ ID NO: 22) and X17069 (SEQ ID NO: 23), and p59 (SEQ ID NO: 24) a defined component of untransformed steroid receptor complexes. hFKBPS2 shares 51 residues (above alignment) with hFKBP12, conserving 12 (dots) of the 14 residues involved in hydrogen-binding or hydrophobic interactions between hFKBP12 and FK506 or rapamycin. Nine of these residues (all except Arg42, Phe46, and Glu54) are conserved in all 15 sequences aligned here. Asterisk (*) denotes an ambiguous residue; hyphen (-) denotes a gap. (Sc=*S. cerevisiae*; Nc=*N. crassa*).

FIG. 3 depicts the 2167 bp sequence of the hFKBP52 cDNA that contains 99 bp 5' untranslated region (UTR), 1377 bp ORF, and a 691 bp 3'UTR (SEQ ID NO: 25). The deduced hFKBP52 sequence (below ORF) contains 459 residues and predicts a 51.8 kDa protein (SEQ ID NO: 26). Nucleotide and residue positions are on the left, with the initiating ATG as position 1. The TAG stop codon is identified by 3 asterisks (***), and the consensus polyadenylation-cleavage sequence AATAAA (38) is underlined. The hFKBP52 cDNA sequence has been assigned GenBank accession number M88279.

DETAILED DESCRIPTION OF THE INVENTION

A cytosolic protein of mammalian origin of $M_r$ 52,000 has been isolated on the basis of its affinity for FK506, and its partial amino acid sequence has been determined. A corresponding human cDNA has been cloned from a human placental cDNA library, its nucleic acid sequence has been determined and the amino acid sequence of the encoded protein has been deduced. This $M_r$ 52,000 protein is referred to herein as FKBP52 and is a member of a novel class of FK506 binding proteins of varying size and binding capabilities.

As described in detail in Example 1, affinity chromatography using an FK506 affinity matrix was performed to isolate FK506 binding proteins from mammalian tissue samples (specifically, a bovine thymus cytosolic preparation). SDS-PAGE analysis of the eluate revealed that several proteins including the $M_r$ 52,000 protein were retained on the FK506 matrix and released by FK506 in solution.

It should be noted that using SDS-PAGE, this novel immunophilin migrated with an apparent $M_r$ ~55,000. However, as described below, the full-length human cDNA clone was subsequently used to deduce the complete hFKBP52 amino acid sequence. This deduced amino acid sequence has a calculated $M_r$ 51,810. Hence, the novel immunophilin described herein will be termed FKBP52 and referred to as having an $M_r$ 52,000. FKBP52 is similar to other recently identified members of the FKBP family in this respect. The other FKBPs identified include FKBP12, FKBP13 (Jim, Y. L., et al., *Proc. Natl. Acad. Sci. USA*, 88:6677–6681 (1991)), and FKBP25 (Galat, A., et al., *Biochem.*, 31:2427-2434 (1992)). These other FKBPs also each resolve as a larger protein than predicted by cDNA and/or protein sequence. Thus, referring to the novel immunophilin described herein as FKBP52 is consistent with prior convention for naming FKBPs according to their calculated $M_r$s.

As further described in Example 1, N-terminal amino acid sequencing of this $M_r$ 52,000 protein (SEQ ID NO: 1) was performed after electrotransfer of the protein to a PVDF membrane, according to the method described by Matsudaira (Matsudaira, P., *J. Biol. Chem.* 262:10035–10038 (1987)). In addition, internal sequence data (SEQ ID NOS: 2–11) obtained by digestion of nitrocellulose membrane-bound peptide with an appropriate endopeptidase, such as Lysine C, followed by isolation of the resulting peptide fragments using microbore HPLC techniques described by Matsudaira in *A PRACTICAL GUIDE TO PROTEIN AND PEPTIDE PURIFICATION FOR MICROSEQUENCING*, Academic Press (San Diego, Calif., 1989)). In total, 133 amino acids of the sequence of the $M_r$ 52,000 protein have been determined by chemical sequencing. This represents approximately 30% of the complete amino acid sequence.

Enzymatic properties of the $M_r$ 52,000 protein (FKBP52) eluted from the FK506 affinity matrix were assessed using known methods. As described in detail in Example 2, the assay of Harrison and Stein (Harrison, R. K. and R. L. Stein, *Biochemistry* 29:3813–3816 (1990)) can be used to measure peptidyl prolyl cis-trans isomerization (PPIase) activity of FKBP52. Also as described in Example 2, the ability of FK506 to inhibit isomerase activity of FKBP52 was assessed, using standard techniques.

FKBP52 is an active catalyst of the PPIase reaction. Using the peptide substrate Suc-Ala-Leu-Pro-Phe-pNA, the specific activity of FKBP52 is approximately 10% that of recombinant human FKBP12 (rhFKBP12), measuring 3.9× $10^5 M^{-1} s^{-1}$ for FKBP52 and 4.3×$10^6 M^{-1} s^{-1}$ for FKBP12 at 15° C. Both FKBPs have similar selectivities for tetrapeptides differing at the $P_1$ position, with both immunophilins most efficiently catalyzing isomerization of peptides with large hydrophobic residues, such as leucine or phenylalanine, at $P_1$, as shown in Table 1.

TABLE 1

Characterization of hFKBP52 and hFKBP12 as PPIase catalysts of the isomerization of Suc—Ala—P1—Pro—Phe—pNA substrates

| Substrate $P_1$ | Specific activity at 15° C. ($M^{-1}s^{-1}$) | |
|---|---|---|
| | hFKBP12* | hFKBP52 |
| Leu | $4.3 \times 10^6$ | $3.9 \times 10^5$ |
| Phe | $2.0 \times 10^6$ | $7.3 \times 10^4$ |
| Val | $9.0 \times 10^5$ | $3.9 \times 10^4$ |
| Ala | $3.1 \times 10^5$ | $2.6 \times 10^4$ |

*data from Park, S. T., et al., J. Biol. Chem., 267:33126–3324 (1992).

The PPIase activity of hFKBP52 is potently inhibited by FK506 and rapamycin; both drugs are tight-binding inhibitors, with K s of 10 nM and 8 nM, respectively (vs 0.6 nM and 0.25 nM, respectively, for hFKBP12). Importantly, the high affinity of FKBP52 for FK506 and rapamycin reasonably implies that FKBP52 could bind to these ligands at the systemic concentrations (blood levels) achieved during clinical use of these drugs, and that the well-documented spectrum of immunosuppressive effects and/or side-effects of FK506 therapy results, in part, from FKBP52-mediated actions.

To facilitate the isolation and determination of a human cDNA clone encoding the FKBP52 protein, DNA probes were designed as described in Example 3. A computer search was used to screen the GenPept library for peptide sequences matching a consensus pattern derived from five known FKBP12 sequences and the human FKBP13 sequence. Two murine peptides were identified in this manner.

Two DNA oligomers with sequences corresponding to part of the murine cDNA coding for the two peptides identified by the computer search were synthesized. Manually aligning these polypeptides, X17068 (SEQ ID NO: 22) and X17069 (SEQ ID NO: 23), with the 133 residues of bovine FKBP52 revealed a striking degree of sequence similarity, as shown in FIG. 2.

These DNA oligomers were then used as polymerase chain reaction primers to amplify the DNA fragment. This fragment was then cloned into a cloning vector and its DNA sequence determined. This DNA fragment was then excised from the vector, radiolabeled with $^{32}$p, and used to screen a human placental cDNA library (Stratagene, Catalog #936203).

Figure 3:
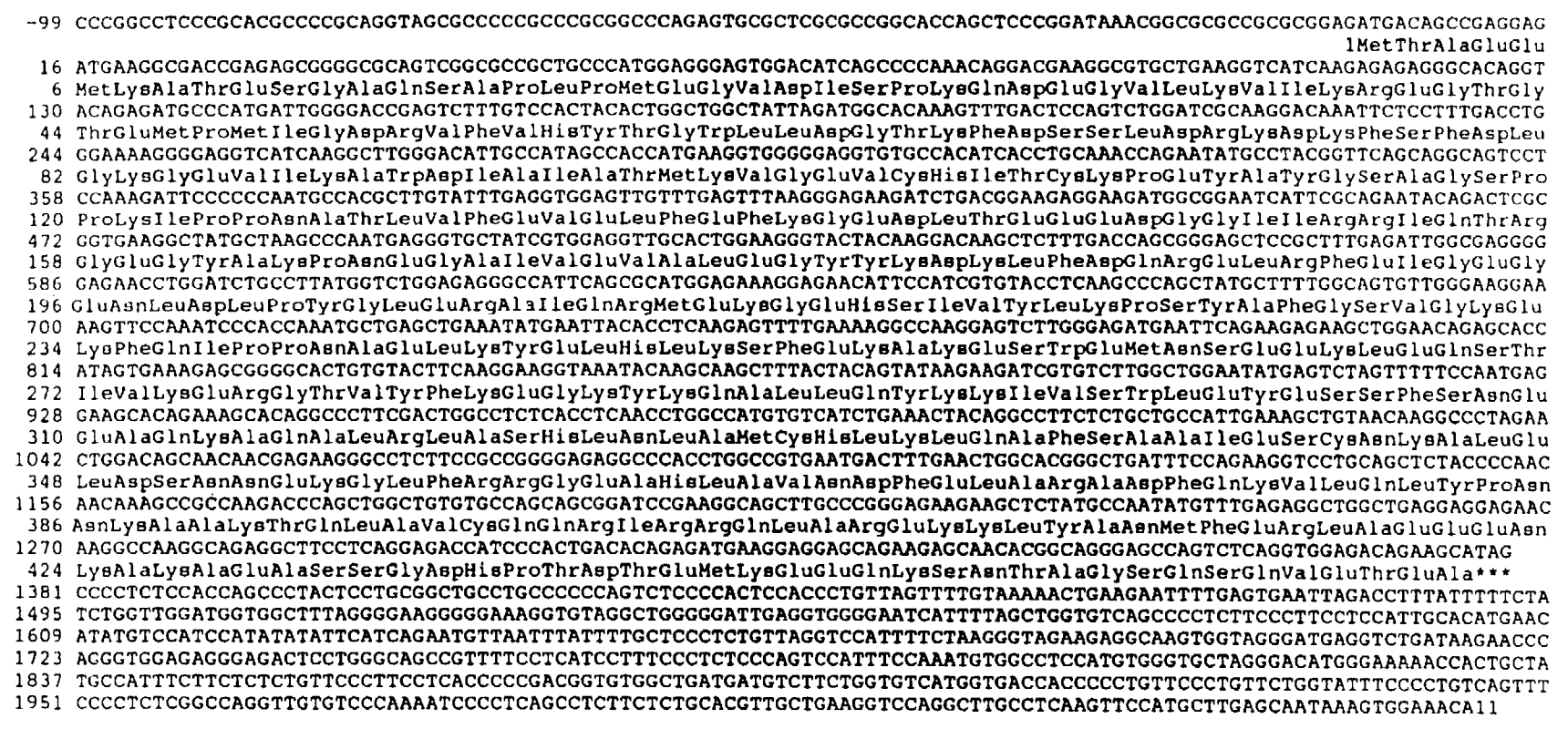

As described in Example 4, a human cDNA clone containing an approximately 2.2 kb insert which hybridizes with a DNA fragment encoding a consensus amino acid sequence present in both FKBP-12 and FKBP-13, has been identified, purified, and sequenced in its entirety. The sequence of the coding strand, which is 2167 bases, is presented in FIG. 3 (SEQ ID NO: 25). The correct open reading frame of the 2.2 kb cDNA sequence was identified (see Example 5) and the deduced amino acid sequence, from amino terminus to carboxyl terminus, is shown in FIG. 3. The deduced protein has 459 amino acids and an $M_r$ of 51,819 (SEQ ID NO: 26).

As described in detail in Example 6, the hFKBP52 open reading frame was expressed in *E. coli* and cleaved and uncleaved proteins were analyzed by gel electrophoresis to confirm the identity of hFKBP52. This recombinant protein migrated with an apparent $M_r$ 55,000, just as native bovine FKBP52.

An alignment of the amino acid sequences, as determined for the bovine $M_r$ 52,000 FK506 binding protein, with the protein sequence predicted from the human cDNA clone, is shown in FIG. 3. Comparison of the amino acid sequences revealed 89.5% sequence identity. Such sequence identity strongly suggests that the protein encoded by the isolated cDNA clone is an FK506 binding protein with characteristics substantially similar to those of the bovine FKBP52.

The original murine probe corresponded to base pairs (bps) 157–690 in the final hFKBP52 cDNA sequence, and was 89% identical to the human sequence, thus explaining its efficiency in selecting the hFKBP52 cDNA. The deduced hFKBP52 residues aligned well with the chemically determined bFKBP52 peptides, verifying the accuracy of the hFKBP52 ORF sequence and suggesting that bFKBP52 can be largely identical to the complete hFKBP52 sequence (FIG. 2). Nine of the ten bovine peptides are 83–100% identical to their human homologs, while one, closest to the carboxyl terminus and perhaps reflecting relaxed structural and/or functional constraints, is 50% identical.

The deduced hFKBP52 sequence is 79% identical to the X17069 polypeptide (452 residues) and 63% identical to the X17068 polypeptide (560 residues), the lower percentage resulting from a 107 amino acid extension at the carboxyl terminus of the X17068 polypeptide (FIG. 2). This indicates that the X17069 polypeptide is probably murine FKBP52 (mFKB52) while the X17068 polypeptide could be an mFKBP52-related protein or a nonexistent polypeptide reflecting a cDNA artifact.

Surprisingly, the hFKBP52 amino terminus is identical to the amino termini of two partially characterized proteins, p56 (Sanchez, E. R., et al., *Biochem.*, 291:5145–5152 (1990)), now termed hsp 56 (Sanchez, E. R., *J. Biol. Chem.*, 265:22067–22070 (1990); Yem, A. W., et al., *J. Biol. Chem.*, 267:2868–2871 (1992)), and a reported 59 kDA immunophilin (Tai, P.-K. K., et al., *Science*, 256:1315–1318 (1992)), both known to associate with the heat shock protein hsp90 in untransformed steroid hormone receptor complexes.

In addition, the deduced hFKBP52 sequence is 91% identical to the predicted sequence (458 residues, in FIG. 2) of p59 (Lebeau, A.-C., et al., *J. Biol. Chem.*, 267:4281–4284 (1992)), a 59 kDa protein that associates with hsp90 in the untransformed rabbit androgen, estradiol, glucocorticoid, and progesterone receptors. Therefore, it is reasonable to predict that these are all the same protein and that the deduced hFKBP52 and p59 sequences reflect the complete sequence of the 56–60 kDA protein found in untransformed mammalian and avian steroid hormone receptor complexes.

Steroid hormones bind to their respective steroid hormone receptors, and transform, or activate, the receptor to a DNA-binding form. (Sanchez, E. R., *J. Biol. Chem.*, 265:22067–22070 (1990)). The untransformed, (in-active, non-DNA-binding) steroid hormone receptor typically comprises a receptor polypeptide associated with a number of heat shock proteins (hsps), with a sedimentation coefficient of approximately 9S. For example, the glucocorticoid receptor is a heterotetramer with one receptor polypeptide, two hsp 90 molecules and one hsp 59 molecule. (Rexin, M. et al., *J. Biol. Chem.*, 266:24601–24605 (1990). Upon binding of steroid hormone to untransformed receptor, the 9 S complex dissociates to a ~4–6S form, which then binds to DNA. As a component of untransformed steroid receptor complexes, FKBP52 could be involved in stabilizing, or blocking, the inactive receptor and this could affect conversion of the receptor to its active, DNA binding, state by binding FK506 and/or rapamycin.

Furthermore, the deduced hFKBP52 sequence reveals a core consensus region when aligned with FKBP12 and other FKBPs. This consensus region lies within the amino terminal portion of hFKBP52, between residues 41–134, and contains 51 residues of conserved identity and position (FIG. 2). The key residues contributing to the high-affinity interaction between hFKBP12 and FK506 corroborate this FKBP12-like core of hFKBP52 and reasonably predict that residues 41–134 define the FK506 - and rapamycin-binding domain of hFKBP52.

The residues critical to the hFKBP12-FK506 interaction, defined by high resolution structural analysis of the complex, and site-directed mutagenesis studies of individual hFKBP12 residues, are highly conserved in the hFKBP52 core region. Thirteen of the fourteen residues involved in hydrogen bonding or hydrophobic interactions between hFKBP12 and FK506 (Tyr26, Phe326, Asp37, Arg42, Phe46, Gln53, Glu54, Val55, Ile56, Trp59, Tyr82, His87, Ile91, and Phe99 in FKBP12) are conserved in FKBP52 (dotted residues, FIG. 2). The high degree with which these crucial residues are conserved reasonably explains why rhFKBP52 displays a high affinity for FK506 and rapamycin and similar substrate specificity profile for PPIase catalysis.

A pattern search alignment algorithm and secondary structure analysis (DNAStar, Inc. software) also corroborate the hFKBP52 homology alignment. Pattern searching, built around the positions and identities of hFKBP12 residues that interact with FK506 and are conserved in different FKBP12 sequences, aligned the FKBP12, p59, and X17069 polypeptide sequences. Secondary structure analysis of the hFKBP52 sequence predicted that the first one-third of the protein contains the FKBP12-like domain. The Trp59 residue of FKBP12, in Van der Waals contact with the pipecolinic moiety of FK506 and completely conserved in all FKBPs (FIG. 2), was a particularly useful benchmark of the latter analysis. In all known members of the FKBP family, this conserved Trp residue is found near the beginning of a short α-helix that follows a short β-sheet.

The 325 residues of hFKBP52 that lie beyond the FKBP12 consensus region reasonably form at least one additional protein domain. Hydrophobic cluster analysis (HCA) has been used to postulate that p59, the rabbit homolog of hFKBP52, has three hsp binding immunophilins (HBI) domains structurally related to FKBP12. They define the first domain, HBI-I, as hFKBP52 residues 32–138 and predict that the second and third domains, HBI-II and HBI-III, correspond to residues 149–253 and 268–372, respectively. The HBI-I domain clearly corresponds well to the core consensus region of residues 41–134 that were defined for hFKBP52 by sequence alignments. Furthermore, the model predicts that the remaining residues of hFKBP52 will be organized as two domains, each with structural similarities to the first.

Given that FK506 and rapamycin bind to untransformed glucocorticoid receptor complexes without displacing the integral components, that FKBP52 associates directly with hsp90 (Renoir, J.-M., et al., *J. Biol. Chem.*, 265:10740–10745 (1990), Rexin, A., et al., *J. Biol. Chem.*, 266: 24601–24605 (1991)), and that FK506 and rapamycin bind directly to FKBP52, it is reasonable to predict the FKBP52 will have at least two structural domains to accommodate these distinct functions. The FKBP12-like consensus region in the first one-third of FKBP52 reasonably defines the immunosuppressant binding domain of the protein, while the remaining residues reasonably constitute the putative hsp90 binding site.

The deduced hFKBP52 sequence contains a variety of consensus motifs that reflect possible post-translational modification(s) and/or functional characteristics of the protein. Consensus motifs typical of asparagine-linked glycoproteins, protein kinase phosphorylation sites, and calmodulin binding domains are present.

Moreover, fourteen protein kinase phosphorylation site elements, representing five classes of motifs, are present in the deduced hFKBP52 sequence. Using asterisks to identify potentially phosphorylated residues and "X" to denote any amino acid, these sites are as follows: $L^{317}RLAS*H$, a multifunctional calmodulin-dependent protein kinase II or S6 kinase II element (XRXXS*X); $I^{25}S*PK$ and $G^{117}S*PP$, a proline-dependent protein kinase motif (XS*PX); $G^{114}SAGS*P$, $W^{259}EMNS*E$, $L^{300}EYES*S$, $E^{393}SSFS*N$, $L^{346}ELDS*N$, $A^{427}EASS*G$ and $E^{442}EQKS*N$, casein kinase I phosphorylation sites (XS (P) XXS*X or XEXXS*X); and $V^{297}S*WLEY$, $F^{306}S*NEEH$, $D^{349}S*NNEK$, and $Q^{452}S*QVET$, sites of casein kinase II (CKII) phosphorylation (XS*XXEX). These motifs suggest that the ~59 kDa immunophilin is phosphorylated and that phosphorylation(s) could produce multiple isoforms. Since hsp90 associates with, and enhances CKII kinase activity of, CKII in cell lysates and in in vivo reconstitution assays, it is reasonable to predict that CKII associates in vivo with an hsp90-FKBP52 complex and phosphorylates one or more serines in both proteins. The putative calmodulin binding domain of p59 (Lebeau, M. C., et al., *J. Biol. Chem.* 267:4281–4284 (1992)), suggests that the seventeen residue stretch Arg399—Phe415 comprises a similar domain in hFKBP52. These residues constitute an amphililic α-helical peptide, a motif common to many calmodulin-binding proteins (O'Neil, K. T., et al., *Trends. Biochem-Sci.*, 15:59–64 (1990)), and suggest that calmodulin and intracellular $Ca^{+2}$ levels could modulate hFKBP52 function.

Thus, as described above, a new member of the class of FK506 binding proteins has been identified and shown to be of approximate $M_r$ 52,000. A human cDNA clone containing a cDNA insert which hybridizes with a DNA fragment encoding a consensus amino acid sequence present in both FKBP12 and FKBP13 has also been obtained and its deduced amino acid sequence has been shown to encode a protein of size $M_r$ 51,810, essentially the same as that of the binding protein isolated by FK506 affinity chromatography ($M_r$ 52,000).

This human cDNA clone can be used to produce an FKBP52 in vitro, such as by introducing the insert into an appropriate expression vector (e.g., pKK223, pOP, pRK5B) and expressing the encoded product in host cells (bacterial, yeast, or mammalian) containing the expression vector. This expressed FKBP52 can be used for a number of diagnostic and therapeutic purposes.

The FKBP52 can be used in screening assays for detection of new naturally occurring immunosuppressant compounds. For example, FKBP52 could be used to screen fermentation broths, produced by known techniques, for compounds that bind to it and, thus, are potential immunosuppressant candidates. Alternately, FKBP52 can be used to screen existing synthetic compounds for binding affinity and subsequent immunosuppressant evaluation. It is reasonable to expect that a compound which binds FKBP52 will be FK506-like and, thus, have immunosuppressive capabilities.

FKBP52 can also be used as the basis for design of FK506-like molecules by determining and characterizing the active binding site(s) of FKBP52, designing a molecule which binds to it (them) and assessing its ability to suppress an immune response.

It is also possible to use the newly identified FKBP52 for diagnostic purposes. For example, FKBP52 can be affixed to a solid support using a variety of chemical coupling techniques which link amino acid residues, such as methionine, lysine, cystine, and tryptophan to inert matrixes, such as Affigel (BioRad) or cyanogen bromide-treated Sepharose (Pharmacia). The FKBP52 bearing solid support is then contacted with tissue extracts or body fluids, such as blood and urine, from individuals receiving FK506 immunosuppressant treatment. Detection and/or quantitation of the parent compound FK506, or its metabolites, can be carried out using known methods, such as spectrophotometric measurement or scintillation counting.

It is also possible to use FKBP52 to identify natural, intracellular FK506-like substances (i.e., molecules or compounds) that function in intrinsic regulatory events in cellular immunity and metabolism. FK506-like substances are defined herein as substances which bind FKBP52 to a similar extent as FK506 under the same conditions under which FK506 binds with FKBP52. Furthermore, FKBP52 can be used to identify natural intracellular substances that may be targets for other novel immunosuppressive agents.

FKBP52 can also be modified in such a way as to enhance its binding capability, and/or other immunosuppressive characteristics. Such modifications (e.g., truncating sequence length) can be carried out using known methods, such as site directed mutagenesis.

Finally, FKBP52 can be used to modify the transformation of steroid hormone receptors. As discussed herein, FKBP52 is common to several vertebrate species and is associated with the 90 kDa heat shock protein (hsp90) in untransformed steroid hormone receptors. Thus, it is reasonable to predict that FKBP52 plays a critical role in the transformation of steroid hormone receptors.

For example, evidence presented herein indicates that FK506 binds tightly to FKBP52. (FKBP52 also binds rapamycin, another immunosuppressive agent). It is also established that certain immunosuppressive treatments (e.g., cyclosporin, which binds to the immunophilin, cyclophilin) result in unpleasant side-effects which can be attributed to an increase in steroid hormone levels. (Paus, R., et al., *Lab. Invest.*, 60:365–369 (1989)). It is reasonable to predict that FK506 binds to FKBP52, which, in turn, transforms a steroid hormone receptor by causing dissociation of the FKBP52 molecule from a steroid hormone receptor complex, such as the androgen receptor. This transformation of the steroid receptor could lead to unwanted side-effects, such as an increase in body hair growth. An antibody to FKBP52 can be co-administered to an individual receiving FK506 therapy to block binding of FK506 to FKBP52 and consequently block the steroid hormone receptor effects transformation. Alternatively, an FK506-like substance, can be used as an antagonist to block FK506 binding to FKBP52.

It is also possible to design an anti-sense nucleotide which will hybridize to the mRNA encoding FKBP52, and inhibit translation of the mRNA to protein. Thus, production of FKBP52 can be decreased, or completely inhibited, thereby decreasing, or eliminating unwanted steroidal side-effects during FK506 or rapamycin therapy.

The present invention will now be illustrated by the following Examples, which are not intended to be limiting in any way.

EXAMPLE 1

Protein Purification and Sequencing

An amino derivative of FK506 at the C32 position was prepared as described in Fretz et al. (Fretz, H. et al., *J. Am. Chem. Soc.* 113:1409–1411 (1991)) and coupled to Affigel 10 resin to yield an FK506 affinity matrix (approximately 1 mg of FK506 coupled per ml of resin). Bovine thymus cytosol extract was prepared as follows: tissues were snap-frozen in liquid nitrogen, and 75 gram amounts were homogenized in 100 mM potassium phosphate, pH 7.4, containing 1 mM PMSF and 5 mM DTT for 60 sec in a Waring blender. The extract was clarified by centrifugations at 40,000× g and then 100,000×g. Cytosol extract was then passed over a 5 ml FK506 affinity column containing an amino acid derivative of FK506 at the C32 position. Flow rate was 0.2 ml/min. The column was washed extensively with phosphate buffered saline containing 0.1% Tween 20 detergent and eluted sequentially with FK506 (200 µg/ml in phosphate buffer) and then 6M guanidine hydrochloride. Eluted proteins were dialyzed extensively against 10 mM Tris, pH 7.0, and aliquots were lyophilized. Approximate molecular weight was determined by SDS-PAGE on a 12½% acrylamide gel using lysozyme (M.W. 14,400), α-chymotrypsin (M.W. 21,500), carbonic anhydrase (M.W. 31,000), ovalbumin (M.U. 45,000) and bovine serum albumin (M.W. 66,000) to calibrate relative migration.

Proteins were visualized by Coomassie blue or silver staining or electroblotted onto either Immobilon-P (0.45 µm pore size, Millipore) or nitrocellulose (Schleicher and Scheull). The proteins transferred to Immobilin-P were visualized by Coomassie blue and used for N-terminal sequencing, described below. Proteins transferred to nitrocellulose were visualized with Ponceau S and used for in situ digestion.

N-terminal amino acid sequencing was performed after electrotransfer to a PVDF membrane as described by Matsudaira, P., *J. Biol. Chem.*, 262:10035 (1987). A band of protein with $M_r$ ~55,000 band was excised from the Immobilin P membrane and loaded directly into an automated sequencer (Applied Biosystems) for amino terminal sequencing. For internal sequence determination, peptide fragments were generated by digest $M_r$ ~55,000 band (on nitrocellulose) with endoproteinase Lysine C (Wako Chemicals, USA) and then separating them by an HPLC system (Hewlett Packard) equipped with a variable wavelength detector and a Vydac C18 2.1×250 mm column. A two-step linear gradient was used to elute the peptides; buffer A was 0.09% trifluoroacetic acid (TFA) in water while buffer B was 0.06% TFA in acetonitrile. Peptides were eluted at a flow rate of 200 µl min$^{-1}$ with a sequence of linear gradients from 5% B at 0 min to 33% B at 65 min, 60% B at 90 min, and 100% B at 105 min. Peaks absorbing at 214 nm were collected in 0.5 ml microcentrifuge tubes and stored immediately without drying at −20° C. For protein sequence determination, the peak fractions were applied to a polybrene precycled glass-fiber filter and placed in the sequencer reaction cartridge. The N-terminal amino acid sequence (SEQ ID NO: 1) and additional internal sequences (SEQ ID NOS: 2–11) of the $M_r$ 52,000 protein are shown in FIG. 1.

EXAMPLE 2

Peptidyl-prolyl Cis-trans Isomerase Assay

The peptidyl-prolyl isomerization rate was determined by coupling isomerization of a prolyl-containing peptide to trans substrate hydrolysis by chymotrypsin (Fisher, G., et al., *Nature* 337:476–478 (1989)). The assay was performed according to Harrison and Stein (*Biochem.*, 29:3813–3816 (1980) with modifications described by Park S. T., et al., *J. Biol. Chem.* 267:3316–3324 (1992). The tetrapeptide substrate succinyl-Ala-P1-Pro-Phe-p-nitroanilide, where P1=Leu, was used to determine specific activity and inhibition constants, and a series of peptide substrates with related structures (P1=Phe, Val, Ala, Gly, Glu or Lys) was used to determine substrate specificity. Protein concentrations of rhFKBP52 stock solutions were determined by a Coomassie Blue binding assay (Bradford, M., *Anal. Biochem.*, 72:248–254 (1976)). FKBP52 (60 nM final) was added to a reaction mixture containing substrate (27 µM final) in 0.1M Tris-HCl, pH 7.8 at 15° C., and the solution was incubated in a 2 ml cuvette for 5 min at 15° C. (950 µl final) before adding chymotrypsin (100 µg ml$^{-1}$ final) to start reaction. For measurement of substrate specificity, the final FKBP52 concentration was adjusted so the $K_{obs}$ was at least four-fold higher than $k_{non-enz}$. Inhibition data were fit to an equation for tight-binding competitive inhibitors using KineTic™ software (BioKin, Ltd.) running on a Macintosh IIcx computer.

EXAMPLE 3

Identification of Murine cDNA Sequences

A computer search was undertaken to identify protein sequences that contain a consensus pattern of conserved residues derived from five FKBP12 sequences (human, murine, bovine, *Saccharomyces cerevisiae* and *Neurospora crassa*) and the human FKBP13 sequence. This consensus pattern (SED ID NO: 32) is as follows:

1G-xxx-xxxx-xxxx-xxxGxxxxxHYxGxLxxGxxFDx-SxxxxxPxxxxxGx-Q-

VIXGWxxGxxxxxGxxxxLxIx-x-xxYGxxxxxxIPxxxTLxFxx-ELx-----Kxx

The residues indicated in upper case letters are specific amino acids, defined by the single letter amino acid code. Each dash (-) indicates a gap introduced into one or more of the protein sequences for optimal alignment. A cross mark (x) represents any amino acid. Of the thirty-one conserved amino acids defined by the consensus pattern, nine Y26, F36, D37, V55, I56, W59, Y82, I91 and F99 (the upper case letter is the amino acid and the number is the position of the residue within human FKBP12) are residues known to interact with FK506 in the human FKBP12/FK506 co-complex (Van Duyne, G. D. et al., *Science* 251:839 (1991)). When a computer search was performed on the translated GenBank database (GenPept) using the above consensus pattern for alignment, the predicted protein products of two murine cDNA sequences (GenBank accession number X17068 and X17069) were identified. These predicted protein products are identical to each other because the first 1300 base pairs (bp) of X17068 and X17069 are identical. X17068 is 1817 bp in length and X17069 is 2046 bp in length. The alignment of the consensus sequence with the homologous portions of the predicted protein products from X17068 (SEQ ID NO: 22) and X17069 (SEQ ID NO: 23) is shown below:

Consensus

G-xxx-xxxx-xxxx-xxxGxxxxxHYxGxLxxGxxFDx-SxxxxxPxxxxxGx-Q-

X17068

G-VLKVIKREGTGTETPMIGDRVFVHYTG-WLLDGTKFDSSLDRKDKFSFDLGK-GE

X17069

G-VLKVIKREGTGTETPMIGDRVFVHYTG-WLLDGTKFDSSLDRKDKFSFDLGK-GE

Consensus

VIxGWxxGxxxxxGxxxLxIx-x-xxYGxxxxxxIPxxxTLxPxxELx
----Kxx

X17068

VIKAWDIAVATMKVGEVCHITCK-PEYAYGAAGSPPKIPP-NATLVFEVELFFEF---KGE

X17069

IKAWDIAVATMKVGEVCHITCK-PEYAYGAAGSPPKIPP-NATLVFEVELFFEF---KGE

The predicted protein products from X17068 and X17069 were also identified by searching the GenPept database directly within the human FKBP12 amino acid sequence (SEQ ID NO: 13). The alignment of the human FKBP12 (hFKBP12) sequence with the homologous portions of the predicted protein products of X17068 and X17069 is shown below:

hFKBP12

GVQVETISPGDGRTFPKRGQTCVVHYTG-MLEDGKKFDSSRDRNKPFKFMLGKQE

X17068

GVLKVIKREGTGTETPMIGDRVFVHYTG-WLLDGTKFDSSLDRKDKFSFDLGKGE

X17069

GVLKVIKREGTGTETPMIGDRVFVHYTG-WLLDGTKFDSSLDRKDKFSFDLGKGE hFKBP12

VIRGWEEGVAQMSVGQRAKLTISP-

DYAYGATGHPGIIPPHATLVFDVELLKLE

X17068

VIKAWDIAVATMKVGEVCHITCK-PEYAYGAAGSPPKIPPNATLVFEVELFFEF

X17069

VIKAWDIAVATMKVGEVCHITCK-PEYAYGAAGSPPKIPPNATLVFEVELFFEF

Of the fifty-four conserved amino acids defined by this alignment, fifteen (Y26, F36, D37, R42, F46, F48, Q53, E54, V55, I56, W59, Y82, H87, I91 and F99) are residues known to interact with FK506 in the human FKBP12-FK506 co-complex (Van Duyne, G. D. et al., 1991)).

EXAMPLE 4

Isolation of Human cDNA Encoding FKBP52

Two short DNA oligomers, each selected from a 1300 bp region of identity within X17068 and X17069 cDNAs, were synthesized as PCR primers. The oligomers SEQ ID NO: 27, forward primer, and SEQ ID NO: 28, reverse primer) were constructed on a DNA synthesizer (Applied Biosystems) and used to amplify an approximate 500 bp fragment from a λZAPII mouse thymus cDNA library (Stratagene Cloning Systems). To amplify the DNA, 2 µl of the library was heated at 80° C. in 33.7 µl of water for 15 min. and the primers (0.4 µM final), reaction buffer, dNTPs, and Ampli-Taq were added according to Gene-Amp PCR reagent kit (Perkin-Elmer Corporation) instructions. The DNA was amplified in a thermocycler (Eppendorf) for 35 rounds (cycles of 94° C. for 1 min, 58° C. for 2 min, 72° C. for 2 min), and the resultant fragment was resolved on a 3% agarose gel (NuSieve 3:1, FMC Bioproducts), transferred to GeneScreen (DuPont-New England Nuclear), and hybridized with a radiolabeled oligomer SEQ ID NO: 29 that was predicted from the X17068 and X17069 sequences to be internal to the fragment. When autoradiography demonstrated specific hybridization, the fragment was cloned into pCR1000 (Invitrogen Corporation), and competent E. coli DH5α was transformed and plated. The cloned insert (positive colony identified by hybridization), corresponding exactly to a 534 bp portion of the murine cDNAs (nucleotides 40–573 in X17068 and X17069), was sequenced with a Sequenase Version 2.0 DNA sequencing kit (US Biochemicals).

The fragment was excised with EcoR I and Hind III (all restriction enzymes from New England BioLabs), radiolabeled with $^{32}P$ dCTP, and used as a hybridization probe for library screening. Eighteen clones were selected by screening 4×10$^5$ plaques of a human placenta λZAPII cDNA library (Stratagene) under stringent conditions. Fifteen clones were rescreened, and the inserts of twelve were excised to produce pBluescript (Stratagene) subclones for sequence analysis. Purified DNA from each clone was digested with Sac I and Kpn I, and insert sizes were determined by agarose gel electrophoresis. Partial nucleotide sequences of each insert were determined with universal sequencing primers and the Sequenase kit. A human FKBP52 (hRKBP52) cDNA clone containing an approximate 2.2 kilobase (kb) insert with 73% identity to the X17068 and X17069 nucleotide sequences was purified and sequenced in its entirety. The sequence of the coding strand of the human cDNA clone, from 5' to 3', is shown in FIG. 3 (SEQ ID NO: 25).

The sequence is 2167 bases in length. The ATG initiation codon and the TAG stop codon for the deduced protein product are underlined.

EXAMPLE 5

Deduced Amino Acid Sequence from the Human cDNA Clone

The correct open reading frame of the human cDNA sequence was identified by comparing the possible translation products to (1) the determined peptide sequences from the bovine thymus $M_r$ 52,000 protein and 2) the deduced amino acid sequences of the murine cDNAs identified by computer search. The deduced amino acid sequence, from amino terminus to carboxyl terminus, of the human protein is shown in FIG. 3 (SEQ ID NO: 26).

EXAMPLE 6

Expression and Purification of Human FKB52 From *E. Coli*

The hFKBP52 open reading frame (ORF) was expressed in *E. coli* with a vector (pQE8, Qiagen Inc.) that expresses recombinant proteins with an amino terminal histidine tag that facilitates protein purification via $Ni^{2+}$ affinity chromatography. By modifying the 5' end of the hFKBP52 ORF to encode a cleavage site, we could use Factor Xa to remove the tag and cleavage site from the recombinant hFKBP52 (rhFKBP52). Synthetic oligomers were used as PCR primers to modify and amplify the ORF. The forward primer, SEQ ID NO: 30, included a BamHI site (GGATCC), nucleotides encoding the Factor Xa cleavage site (ATCGAGGGTAGA to encode Ile-Glu-Gly-Arg), and the first nineteen nucleotides of the hFKBP52 ORF (ATGACAGCCGAGGAGATGA). The reverse primer, SEQ ID NO: 31, included a Hind III site (AAGCTT) and the complement of a stop codon (TTA) followed by the complement of the last sixteen nucleotides of the hFKBP52 ORF (TGCTTCTGTCTCCACC).

The ORF was amplified from the hFKBP52 insert by 10 rounds of PCR (5 min denaturation at 94° C. for 1 min, 72° C. for 2 min, final extension at 72° C. for 10 min) in a thermocycler (Perkin Elmer Corporation), and the resultant DNA fragment was digested with BamH I and Hind III, cloned into the BamH I and Hind III sites of pQE8, and used to transform *E. coli* XA90 (the kind gift of J. Wang, Harvard University). A 500 ml volume of Luria broth (100 µg ml$^{-1}$ amplicillin) was inoculated with a positive colony, and the culture was grown at 37° C. to OD$_{600}$ 0.6. IPTG (isopropyl-β-D-thiogalactopyranoside) was added to 2 mM, and the cells were grown for an additional 2 hr before harvesting by centrifugation (4,000×g, 20 min, 4° C). The cells were lysed by stirring for 1 hr at room temperature in 6M guanidine HCl, 0.1M NaH$_2$PO$_4$, 10 mM Tris adjusted to pH 8.0 with NaOH, and the lysate was cleared by centrifugation (10,000×g, 15 min, 4° C.) and applied to an 8 ml $Ni^{2+}$-NTA-agarose (Qiagen Inc.) affinity column. rhFKBP52 was eluted from the column according to the manufacturer's instructions and was refolded by dialysis against Factor Xa buffer (0.1M NaCl, 50 mM Tris-HCl, pH 8.0, 1 mM CaCl$_2$) for 3 hr at 4° C. The amino terminal tag was removed by dissolving ~30 µg of lyophilized Factor Xa (Boehringer Mannheim Biochemicals) in 5 ml of the refolded protein and then dialyzing twice overnight at 4° C. against Factor Xa buffer. Cleaved and uncleaved protein was analyzed by gel electrophoresis and amino terminal sequencing to confirm the identity of the rhFKB52.

EQUIVALENTS

Those skilled in the art will recognize, or be able to ascertain using no more than routine experimentation, many equivalents to the specific embodiments of the invention described herein. Such equivalents are intended to be encompassed by the following claims.

Statement Regarding the Content of the Sequence Listing in Paper and Computer Readable Form The content of the Sequence Listing in paper form and of the computer readable form are the same.

We claim:

1. A recombinant DNA molecule comprising a DNA sequence which encodes a $M_r$ 52,000 protein of human origin which binds FK506, wherein said DNA sequence is the nucleotide sequence SEQ ID NO: 25.

2. An isolated DNA sequence encoding a $M_r$ 52,000 protein of human origin which binds FK506, wherein said DNA sequence is the nucleotide sequence SEQ ID NO: 25.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Thr Ala Glu Glu Thr Lys Ala Ala Glu Ser Gly Ala Gln Ser Ala Pro
  1               5                  10                  15

Leu Arg Leu Glu Gly Val Asp Ile Ser Pro Lys
                20                  25
```

( 2 ) INFORMATION FOR SEQ ID NO:2:

( i ) SEQUENCE CHARACTERISTICS:
  ( A ) LENGTH: 9 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

Asp Arg Phe Ser Phe Asp Leu Gly Lys
1               5

( 2 ) INFORMATION FOR SEQ ID NO:3:

( i ) SEQUENCE CHARACTERISTICS:
  ( A ) LENGTH: 8 amino acids
  ( B ) TYPE: amino acid
  ( D ) TOPOLOGY: linear ( i i ) MOLECULE TYPE: protein ( x i ) SEQUENCE DESCRIPTION: SEQ ID NO:3:

Ala Xaa Asp Ile Ala Val Ala Thr
1               5

( 2 ) INFORMATION FOR SEQ ID NO:4:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

Met Lys Val Gly Glu Val Xaa His Ile Thr Cys Lys
1               5                   10

( 2 ) INFORMATION FOR SEQ ID NO:5:

( i ) SEQUENCE CHARACTERISTICS:
  ( A ) LENGTH: 17 amino acids
  ( B ) TYPE: amino acid
  ( D ) TOPOLOGY: linear ( i i ) MOLECULE TYPE: protein ( x i ) SEQUENCE DESCRIPTION: SEQ ID NO:5:

Ile Pro Pro Asn Ala Thr Leu Val Phe Glu Val Glu Leu Phe Glu Phe
1               5                   10                  15

Lys ( 2 ) INFORMATION FOR SEQ ID NO:6:

( i ) SEQUENCE CHARACTERISTICS:
  ( A ) LENGTH: 16 amino acids
  ( B ) TYPE: amino acid
  ( D ) TOPOLOGY: linear ( i i ) MOLECULE TYPE: protein ( x i ) SEQUENCE DESCRIPTION: SEQ ID NO:6:

Pro Asn Glu Gly Ala Leu Val Glu Val Ala Leu Glu Xaa Tyr Phe Gln
1               5                   10                  15

( 2 ) INFORMATION FOR SEQ ID NO:7:

( i ) SEQUENCE CHARACTERISTICS:
  ( A ) LENGTH: 6 amino acids (B) TYPE: amino acid
        (D) TOPOLOGY: linear (ii) MOLECULE TYPE: protein (xi) SEQUENCE DESCRIPTION: SEQ ID NO:7:

Tyr Glu Ile His Leu Lys
    1               5

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:8:

Gly Thr Val Tyr Phe Lys
    1               5

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:9:

Ala Leu Glu Leu Asp Ser Asn Asn Glu Lys
    1               5                   10

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:10:

Leu Tyr Ala Asn Met Phe Glu Leu Ala Ala Glu Glu Glu Xaa Lys
    1               5                   10                  15

(2) INFORMATION FOR SEQ ID NO:11:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:11:

Ala Leu Val Ala Ala Gly Asp Gln Pro Ala Asp Ala Glu Met Arg Asp
    1               5                   10                  15

Glu Pro (2) INFORMATION FOR SEQ ID NO:12:

(i) SEQUENCE CHARACTERISTICS:
        (A) LENGTH: 459 amino acids
        (B) TYPE: amino acid
        (D) TOPOLOGY: linear ( i i ) MOLECULE TYPE: protein ( x i ) SEQUENCE DESCRIPTION: SEQ ID NO:12:

| Met<br>1 | Thr | Ala | Glu | Glu<br>5 | Met | Lys | Ala | Thr | Glu<br>10 | Ser | Gly | Ala | Gln | Ser<br>15 | Ala |
|---|---|---|---|---|---|---|---|---|---|---|---|---|---|---|---|
| Pro | Leu | Pro | Met<br>20 | Glu | Gly | Val | Asp | Ile<br>25 | Ser | Pro | Lys | Gln | Asp<br>30 | Glu | Gly |
| Val | Leu | Lys<br>35 | Val | Ile | Lys | Arg | Glu<br>40 | Gly | Thr | Gly | Thr | Glu<br>45 | Met | Pro | Met |
| Ile | Gly<br>50 | Asp | Arg | Val | Phe | Val<br>55 | His | Tyr | Thr | Gly | Trp<br>60 | Leu | Leu | Asp | Gly |
| Thr<br>65 | Lys | Phe | Asp | Ser | Ser<br>70 | Leu | Asp | Arg | Lys | Asp<br>75 | Lys | Phe | Ser | Phe | Asp<br>80 |
| Leu | Gly | Lys | Gly | Glu<br>85 | Val | Ile | Lys | Ala | Trp<br>90 | Asp | Ile | Ala | Ile | Ala<br>95 | Thr |
| Met | Lys | Val | Gly<br>100 | Glu | Val | Cys | His | Ile<br>105 | Thr | Cys | Lys | Pro | Glu<br>110 | Tyr | Ala |
| Tyr | Gly | Ser<br>115 | Ala | Gly | Ser | Pro | Pro<br>120 | Lys | Ile | Pro | Pro | Asn<br>125 | Ala | Thr | Leu |
| Val | Phe<br>130 | Glu | Val | Glu | Leu | Phe<br>135 | Glu | Phe | Lys | Gly | Glu<br>140 | Asp | Leu | Thr | Glu |
| Glu<br>145 | Glu | Asp | Gly | Gly | Ile<br>150 | Ile | Arg | Arg | Ile | Gln<br>155 | Thr | Arg | Gly | Glu | Gly<br>160 |
| Tyr | Ala | Lys | Pro | Asn<br>165 | Glu | Gly | Ala | Ile | Val<br>170 | Glu | Val | Ala | Leu | Glu<br>175 | Gly |
| Tyr | Tyr | Lys | Asp<br>180 | Lys | Leu | Phe | Asp | Gln<br>185 | Arg | Glu | Leu | Arg | Phe<br>190 | Glu | Ile |
| Gly | Glu | Gly<br>195 | Glu | Asn | Leu | Asp | Leu<br>200 | Pro | Tyr | Gly | Leu | Glu<br>205 | Arg | Ala | Ile |
| Gln | Arg<br>210 | Met | Glu | Lys | Gly | Glu<br>215 | His | Ser | Ile | Val | Tyr<br>220 | Leu | Lys | Pro | Ser |
| Tyr<br>225 | Ala | Phe | Gly | Ser | Val<br>230 | Gly | Lys | Glu | Lys | Phe<br>235 | Gln | Ile | Pro | Pro | Asn<br>240 |
| Ala | Glu | Leu | Lys | Tyr<br>245 | Glu | Leu | His | Leu | Lys<br>250 | Ser | Phe | Glu | Lys | Ala<br>255 | Lys |
| Glu | Ser | Trp | Glu<br>260 | Met | Asn | Ser | Glu | Glu<br>265 | Lys | Leu | Glu | Gln | Ser<br>270 | Thr | Ile |
| Val | Lys | Glu<br>275 | Arg | Gly | Thr | Val | Tyr<br>280 | Phe | Lys | Glu | Gly | Lys<br>285 | Tyr | Lys | Gln |
| Ala | Leu<br>290 | Leu | Gln | Tyr | Lys | Lys<br>295 | Ile | Val | Ser | Trp | Leu<br>300 | Glu | Tyr | Glu | Ser |
| Ser<br>305 | Phe | Ser | Asn | Glu | Glu<br>310 | Ala | Gln | Lys | Ala | Gln<br>315 | Ala | Leu | Arg | Leu | Ala<br>320 |
| Ser | His | Leu | Asn | Leu<br>325 | Ala | Met | Cys | His | Leu<br>330 | Lys | Leu | Gln | Ala | Phe<br>335 | Ser |
| Ala | Ala | Ile | Glu<br>340 | Ser | Cys | Asn | Lys | Ala<br>345 | Leu | Glu | Leu | Asp | Ser<br>350 | Asn | Asn |
| Glu | Lys | Gly<br>355 | Leu | Phe | Arg | Arg | Gly<br>360 | Glu | Ala | His | Leu | Ala<br>365 | Val | Asn | Asp |
| Phe | Glu<br>370 | Leu | Ala | Arg | Ala | Asp<br>375 | Phe | Gln | Lys | Val | Leu<br>380 | Gln | Leu | Tyr | Pro |
| Asn<br>385 | Asn | Lys | Ala | Ala | Lys<br>390 | Thr | Gln | Leu | Ala | Val<br>395 | Cys | Gln | Gln | Arg | Ile<br>400 |
| Arg | Arg | Gln | Leu | Ala | Arg | Glu | Lys | Lys | Leu | Tyr | Ala | Asn | Met | Phe | Glu |

5,763,590

21                                                                                           22

-continued

|   | 405 | | | | | | 410 | | | | | 415 | |
|---|---|---|---|---|---|---|---|---|---|---|---|---|---|
| Arg | Leu | Ala | Glu<br>420 | Glu | Glu | Asn | Lys | Ala<br>425 | Lys | Ala | Glu | Ala | Ser<br>430 | Ser | Gly |
| Asp | His | Pro<br>435 | Thr | Asp | Thr | Glu | Met<br>440 | Lys | Glu | Glu | Gln | Lys<br>445 | Ser | Asn | Thr |
| Ala | Gly<br>450 | Ser | Gln | Ser | Gln | Val<br>455 | Glu | Thr | Glu | Ala | | | | | |

( 2 ) INFORMATION FOR SEQ ID NO:13:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Gly<br>1 | Val | Gln | Val | Glu<br>5 | Thr | Ile | Ser | Pro | Gly<br>10 | Asp | Gly | Arg | Thr | Phe<br>15 | Pro |
| Lys | Arg | Gly | Gln<br>20 | Thr | Cys | Val | Val | His<br>25 | Tyr | Thr | Gly | Met | Leu<br>30 | Glu | Asp |
| Gly | Lys | Lys<br>35 | Phe | Asp | Ser | Ser | Arg<br>40 | Asp | Arg | Asn | Lys | Pro<br>45 | Phe | Lys | Phe |
| Met | Leu<br>50 | Gly | Lys | Gln | Glu | Val<br>55 | Ile | Arg | Gly | Trp | Glu<br>60 | Glu | Gly | Val | Ala |
| Gln<br>65 | Met | Ser | Val | Gly | Gln<br>70 | Arg | Ala | Lys | Leu | Thr<br>75 | Ile | Ser | Pro | Asp | Tyr<br>80 |
| Ala | Tyr | Gly | Ala | Thr<br>85 | Gly | His | Pro | Gly | Ile<br>90 | Ile | Pro | Pro | His | Ala<br>95 | Thr |
| Leu | Val | Phe | Asp<br>100 | Val | Glu | Leu | Leu | Lys<br>105 | Leu | Glu | | | | | |

( 2 ) INFORMATION FOR SEQ ID NO:14:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met<br>1 | Gly | Val | Gln | Val<br>5 | Glu | Thr | Ile | Ser | Pro<br>10 | Gly | Asp | Gly | Arg | Thr<br>15 | Phe |
| Pro | Lys | Arg | Gly<br>20 | Gln | Thr | Cys | Val | Val<br>25 | His | Tyr | Thr | Gly | Met<br>30 | Leu | Glu |
| Asp | Gly | Lys<br>35 | Lys | Phe | Asp | Ser | Ser<br>40 | Arg | Asp | Arg | Asn | Lys<br>45 | Pro | Phe | Lys |
| Phe | Thr<br>50 | Leu | Gly | Lys | Gln | Glu<br>55 | Val | Ile | Arg | Gly | Trp<br>60 | Glu | Glu | Gly | Val |
| Ala<br>65 | Gln | Met | Ser | Val | Gly<br>70 | Gln | Arg | Ala | Lys | Leu<br>75 | Ile | Ile | Ser | Ser | Asp<br>80 |
| Tyr | Ala | Tyr | Gly | Ala<br>85 | Thr | Gly | His | Pro | Gly<br>90 | Ile | Ile | Pro | Pro | His<br>95 | Ala |
| Thr | Leu | Val | Phe<br>100 | Asp | Val | Glu | Leu | Leu<br>105 | Lys | Leu | Glu | | | | |

( 2 ) INFORMATION FOR SEQ ID NO:15:

(i) SEQUENCE CHARACTERISTICS:
  (A) LENGTH: 107 amino acids
  (B) TYPE: amino acid
  (D) TOPOLOGY: linear (ii) MOLECULE TYPE: protein (xi) SEQUENCE DESCRIPTION: SEQ ID NO:15:

| Gly | Val | Gln | Val | Glu | Thr | Ile | Ser | Pro | Gly | Asp | Gly | Arg | Thr | Phe | Pro |
|---|---|---|---|---|---|---|---|---|---|---|---|---|---|---|---|
| 1 | | | | 5 | | | | | 10 | | | | | 15 | |
| Lys | Arg | Gly | Gln | Thr | Cys | Val | Val | His | Tyr | Thr | Gly | Met | Leu | Glu | Asp |
| | | | 20 | | | | | 25 | | | | | 30 | | |
| Gly | Lys | Lys | Phe | Asp | Ser | Ser | Arg | Asp | Arg | Asn | Lys | Pro | Phe | Lys | Phe |
| | | 35 | | | | | 40 | | | | | 45 | | | |
| Val | Leu | Gly | Lys | Gln | Glu | Val | Ile | Arg | Gly | Trp | Glu | Glu | Gly | Val | Ala |
| | 50 | | | | | 55 | | | | | 60 | | | | |
| Gln | Met | Ser | Val | Gly | Gln | Arg | Ala | Lys | Leu | Thr | Ile | Ser | Pro | Asp | Tyr |
| 65 | | | | | 70 | | | | | 75 | | | | | 80 |
| Ala | Tyr | Gly | Ala | Thr | Gly | His | Pro | Gly | Ile | Ile | Pro | Pro | Asn | Ala | Thr |
| | | | | 85 | | | | | 90 | | | | | 95 | |
| Leu | Ile | Phe | Asp | Val | Glu | Leu | Leu | Lys | Leu | Glu |
|---|---|---|---|---|---|---|---|---|---|---|
| | | | 100 | | | | | 105 | | |

(2) INFORMATION FOR SEQ ID NO:16:

(i) SEQUENCE CHARACTERISTICS:
  (A) LENGTH: 114 amino acids
  (B) TYPE: amino acid
  (D) TOPOLOGY: linear (ii) MOLECULE TYPE: protein (xi) SEQUENCE DESCRIPTION: SEQ ID NO:16:

| Met | Ser | Glu | Val | Ile | Glu | Gly | Asn | Val | Lys | Ile | Asp | Arg | Ile | Ser | Pro |
|---|---|---|---|---|---|---|---|---|---|---|---|---|---|---|---|
| 1 | | | | 5 | | | | | 10 | | | | | 15 | |
| Gly | Asp | Gly | Ala | Thr | Phe | Pro | Lys | Thr | Gly | Asp | Leu | Val | Thr | Ile | His |
| | | | | 20 | | | | | 25 | | | | | 30 | |
| Tyr | Thr | Gly | Thr | Leu | Glu | Asn | Gly | Gln | Lys | Phe | Asp | Ser | Ser | Val | Asp |
| | | | 35 | | | | | 40 | | | | | 45 | | |
| Arg | Gly | Ser | Pro | Phe | Gln | Cys | Asn | Ile | Gly | Val | Gly | Gln | Val | Ile | Lys |
| | 50 | | | | | 55 | | | | | 60 | | | | |
| Gly | Trp | Asp | Val | Gly | Ile | Pro | Lys | Leu | Ser | Val | Gly | Glu | Lys | Ala | Arg |
| 65 | | | | | 70 | | | | | 75 | | | | | 80 |
| Leu | Thr | Ile | Pro | Gly | Pro | Tyr | Ala | Tyr | Gly | Pro | Arg | Gly | Phe | Pro | Gly |
| | | | | 85 | | | | | 90 | | | | | 95 | |
| Leu | Ile | Pro | Pro | Asn | Ser | Thr | Leu | Val | Phe | Asp | Val | Glu | Leu | Leu | Lys |
| | | | 100 | | | | | 105 | | | | | 110 | | |
| Val | Asn |

(2) INFORMATION FOR SEQ ID NO:17:

(i) SEQUENCE CHARACTERISTICS:
  (A) LENGTH: 120 amino acids
  (B) TYPE: amino acid
  (D) TOPOLOGY: linear (ii) MOLECULE TYPE: protein (xi) SEQUENCE DESCRIPTION: SEQ ID NO:17:

| Met | Thr | Ile | Pro | Gln | Leu | Asp | Gly | Leu | Gln | Ile | Glu | Val | Gln | Gln | Glu |
|---|---|---|---|---|---|---|---|---|---|---|---|---|---|---|---|
| 1 | | | | 5 | | | | | 10 | | | | | 15 | |

|     |     |     |     |     |     |     |     |     |     |     |     |     |     |     |
|-----|-----|-----|-----|-----|-----|-----|-----|-----|-----|-----|-----|-----|-----|-----|
| Gly | Gln | Gly | Thr<br>20 | Arg | Glu | Thr | Arg<br>25 | Arg | Gly | Asp | Asn | Val<br>30 | Asp | Val | His |
| Tyr | Lys | Gly<br>35 | Val | Leu | Thr | Ser | Gly<br>40 | Lys | Lys | Phe | Asp | Ala<br>45 | Ser | Tyr | Asp |
| Arg | Gly<br>50 | Glu | Pro | Leu | Asn | Phe<br>55 | Thr | Val | Gly | Gln | Gly<br>60 | Gln | Val | Ile | Lys |
| Gly<br>65 | Trp | Asp | Glu | Gly | Leu<br>70 | Leu | Gly | Met | Lys | Ile<br>75 | Gly | Glu | Lys | Arg | Lys<br>80 |
| Leu | Thr | Ile | Ala | Pro<br>85 | His | Leu | Ala | Tyr | Gly<br>90 | Asn | Arg | Ala | Val | Gly<br>95 | Gly |
| Ile | Ile | Pro | Ala<br>100 | Asn | Ser | Thr | Leu | Ile<br>105 | Phe | Glu | Thr | Glu | Leu<br>110 | Val | Gly |
| Ile | Lys | Gly<br>115 | Val | Gln | Lys | Gly | Glu<br>120 |     |     |     |     |     |     |     |     |

(2) INFORMATION FOR SEQ ID NO:18:

(i) SEQUENCE CHARACTERISTICS:
      (A) LENGTH: 142 amino acids
      (B) TYPE: amino acid
      (D) TOPOLOGY: linear (ii) MOLECULE TYPE: protein (xi) SEQUENCE DESCRIPTION: SEQ ID NO:18:

|     |     |     |     |     |     |     |     |     |     |     |     |     |     |     |     |
|-----|-----|-----|-----|-----|-----|-----|-----|-----|-----|-----|-----|-----|-----|-----|-----|
| Met<br>1 | Arg | Leu | Ser | Trp<br>5 | Phe | Arg | Val | Leu | Thr<br>10 | Val | Leu | Ser | Ile | Cys<br>15 | Leu |
| Ser | Ala | Val | Ala<br>20 | Thr | Ala | Thr | Gly | Ala<br>25 | Glu | Gly | Lys | Arg | Lys<br>30 | Leu | Gln |
| Ile | Gly | Val<br>35 | Lys | Lys | Arg | Val | Asp<br>40 | His | Cys | Pro | Ile | Lys<br>45 | Ser | Arg | Lys |
| Gly | Asp<br>50 | Val | Leu | His | Met | His<br>55 | Tyr | Thr | Gly | Lys | Leu<br>60 | Glu | Asp | Gly | Thr |
| Glu<br>65 | Phe | Asp | Ser | Ser | Leu<br>70 | Pro | Gln | Asn | Gln | Pro<br>75 | Phe | Val | Phe | Ser | Leu<br>80 |
| Gly | Thr | Gly | Gln | Val<br>85 | Ile | Lys | Gly | Trp | Asp<br>90 | Gln | Gly | Leu | Leu | Gly<br>95 | Met |
| Cys | Glu | Gly | Glu<br>100 | Lys | Arg | Lys | Leu | Val<br>105 | Ile | Pro | Ser | Glu | Leu<br>110 | Gly | Tyr |
| Gly | Glu | Arg<br>115 | Gly | Ala | Pro | Pro | Lys<br>120 | Ile | Pro | Gly | Gly | Ala<br>125 | Thr | Leu | Val |
| Phe | Glu<br>130 | Val | Glu | Leu | Leu | Lys<br>135 | Ile | Glu | Arg | Arg | Thr<br>140 | Glu | Leu |     |     |

(2) INFORMATION FOR SEQ ID NO:19:

(i) SEQUENCE CHARACTERISTICS:
      (A) LENGTH: 88 amino acids
      (B) TYPE: amino acid
      (D) TOPOLOGY: linear (ii) MOLECULE TYPE: protein (xi) SEQUENCE DESCRIPTION: SEQ ID NO:19:

|     |     |     |     |     |     |     |     |     |     |     |     |     |     |     |     |
|-----|-----|-----|-----|-----|-----|-----|-----|-----|-----|-----|-----|-----|-----|-----|-----|
| Thr<br>1 | Gly | Thr | Glu | Gly<br>5 | Lys | Arg | Lys | Leu | Gln<br>10 | Ile | Gly | Val | Lys | Lys<br>15 | Arg |
| Val | Asp | His | Cys<br>20 | Pro | Ile | Lys | Ser | Arg<br>25 | Lys | Gly | Asp | Val | Leu<br>30 | His | Met |
| His | Tyr | Thr<br>35 | Gly | Lys | Leu | Glu | Asp<br>40 | Gly | Thr | Glu | Phe | Asp<br>45 | Ser | Ser | Leu |

```
Pro  Gln  Asn  Gln  Pro  Phe  Val  Phe  Ser  Leu  Gly  Thr  Gly  Gln  Val  Ile
     50                      55                      60

Lys  Glu  Gly  Glu  Lys  Arg  Lys  Leu  Val  Ile  Pro  Ser  Glu  Leu  Gly  Tyr
65                       70                      75                          80

Gly  Glu  Arg  Gly  Ala  Pro  Pro  Lys
                    85
```

(2) INFORMATION FOR SEQ ID NO:20:

(i) SEQUENCE CHARACTERISTICS:
      (A) LENGTH: 135 amino acids
      (B) TYPE: amino acid
      (D) TOPOLOGY: linear (ii) MOLECULE TYPE: protein (xi) SEQUENCE DESCRIPTION: SEQ ID NO:20:

```
Met  Met  Phe  Asn  Ile  Tyr  Leu  Phe  Val  Thr  Phe  Phe  Ser  Thr  Ile  Leu
1                     5                     10                      15

Ala  Gly  Ser  Leu  Ser  Asp  Leu  Glu  Ile  Gly  Ile  Ile  Lys  Arg  Ile  Pro
              20                      25                      30

Val  Glu  Asp  Cys  Leu  Ile  Lys  Ala  Met  Pro  Gly  Asp  Lys  Val  Lys  Val
              35                      40                      45

His  Tyr  Thr  Gly  Ser  Leu  Leu  Glu  Ser  Gly  Thr  Val  Phe  Asp  Ser  Ser
     50                      55                      60

Tyr  Ser  Arg  Gly  Ser  Pro  Ile  Ala  Phe  Glu  Leu  Gly  Val  Gly  Arg  Val
65                       70                      75                          80

Ile  Lys  Gly  Trp  Asp  Gln  Gly  Val  Ala  Gly  Met  Cys  Val  Gly  Glu  Lys
                    85                      90                          95

Arg  Lys  Leu  Gln  Ile  Pro  Ser  Ser  Leu  Ala  Tyr  Gly  Glu  Arg  Gly  Val
               100                     105                     110

Pro  Gly  Val  Ile  Pro  Pro  Ser  Ala  Asp  Leu  Val  Phe  Asp  Val  Glu  Leu
               115                     120                     125

Val  Asp  Val  Lys  Ser  Ala  Ala
     130                     135
```

(2) INFORMATION FOR SEQ ID NO:21:

(i) SEQUENCE CHARACTERISTICS:
      (A) LENGTH: 145 amino acids
      (B) TYPE: amino acid
      (D) TOPOLOGY: linear (ii) MOLECULE TYPE: protein (xi) SEQUENCE DESCRIPTION: SEQ ID NO:21:

```
Lys  Val  Ser  Glu  Gln  Val  Lys  Asn  Val  Lys  Leu  Asn  Glu  Asp  Lys  Pro
1                     5                     10                      15

Lys  Glu  Thr  Lys  Ser  Glu  Glu  Thr  Leu  Asp  Glu  Gly  Pro  Pro  Lys  Tyr
              20                      25                      30

Thr  Lys  Ser  Val  Leu  Lys  Lys  Gly  Asp  Lys  Thr  Asn  Phe  Pro  Lys  Lys
              35                      40                      45

Gly  Asp  Val  Val  His  Cys  Trp  Tyr  Thr  Gly  Thr  Leu  Gln  Asp  Gly  Thr
     50                      55                      60

Val  Phe  Asp  Thr  Asn  Ile  Gln  Thr  Ser  Ala  Lys  Lys  Lys  Lys  Asn  Ala
65                       70                      75                          80

Lys  Pro  Leu  Ser  Phe  Lys  Val  Gly  Val  Gly  Lys  Val  Ile  Arg  Gly  Trp
                    85                      90                          95

Asp  Glu  Ala  Leu  Leu  Thr  Met  Ser  Lys  Gly  Glu  Lys  Ala  Arg  Leu  Glu
```

|   |   |   |   |   |   |   |   | 100 |   |   |   |   | 105 |   |   |   |   | 110 |   |   |
|---|---|---|---|---|---|---|---|---|---|---|---|---|---|---|---|---|---|---|---|---|

Ile Glu Pro Glu Trp Ala Tyr Gly Lys Lys Gly Gln Pro Asp Ala Lys
        115                     120                   125

Ile Pro Pro Asn Ala Lys Leu Thr Phe Glu Val Glu Leu Val Asp Ile
130                     135                   140

Asp

145

( 2 ) INFORMATION FOR SEQ ID NO:22:

( i ) SEQUENCE CHARACTERISTICS:
      ( A ) LENGTH: 560 amino acids
      ( B ) TYPE: amino acid
      ( D ) TOPOLOGY: linear ( i i ) MOLECULE TYPE: protein ( x i ) SEQUENCE DESCRIPTION: SEQ ID NO:22:

Ala Arg Gly Gly Gly Glu Arg Gly Ala Val Gly Val Pro Leu Glu Gly
1                  5                     10                15

Val Asp Ile Ser Pro Lys Gln Asp Glu Gly Val Leu Lys Val Ile Lys
               20                  25                  30

Arg Glu Gly Thr Gly Thr Glu Thr Pro Met Ile Gly Asp Arg Val Phe
          35                 40                  45

Val His Tyr Thr Gly Trp Leu Leu Asp Gly Thr Lys Phe Asp Ser Ser
   50                   55                  60

Leu Asp Arg Lys Asp Lys Phe Ser Phe Asp Leu Gly Lys Gly Glu Val
65                   70                  75              80

Ile Lys Ala Trp Asp Ile Ala Val Ala Thr Met Lys Val Gly Glu Val
               85                  90                  95

Cys His Ile Thr Cys Lys Pro Glu Tyr Ala Tyr Gly Ala Ala Gly Ser
          100                105                  110

Pro Pro Lys Ile Pro Pro Asn Ala Thr Leu Val Phe Glu Val Glu Leu
        115                120                  125

Phe Glu Phe Lys Gly Glu Asp Leu Thr Glu Glu Glu Asp Gly Gly Ile
130                   135                  140

Ile Arg Arg Ile Arg Leu Gly Val Lys Ala Met Gln Gly Pro Asn Asp
145                   150                  155              160

Gly Ala Met Val Glu Val Ala Leu Glu Gly Tyr His Lys Asp Arg Leu
             165                170              175

Phe Asp Gln Arg Glu Leu Cys Phe Glu Val Gly Glu Gly Glu Ser Leu
          180              185                  190

Asp Leu Pro Cys Ala Trp Arg Arg Pro Phe Ser Ala Trp Arg Lys Glu
       195                200                205

Ser Ile Pro Ser Cys Thr Ser Asn Leu Ala Met Leu Leu Ala Val Trp
210                   215                  220

Gly Arg Arg Gly Ser Arg Ser His Arg Thr Ala Glu Leu Arg Tyr Glu
225                   230                235              240

Val Arg Leu Lys Ser Phe Glu Lys Ala Lys Glu Ser Trp Glu Met Ser
             245                250              255

Ser Ala Arg Ser Trp Ser Arg Ala Thr Tyr Val Lys Glu Arg Gly Thr
         260                265                  270

Ala Tyr Phe Lys Glu Gly Lys Tyr Lys Gln Ala Leu Leu Gln Tyr Lys
       275                280                285

Lys Ile Val Ser Trp Leu Glu Tyr Glu Ser Ser Phe Ser Gly Glu Glu
   290                   295                  300

| | | | | | | | | | | | | | | |
|---|---|---|---|---|---|---|---|---|---|---|---|---|---|---|
| Met<br>305 | Gln | Lys | Val | His<br>310 | Ala | Leu | Arg | Leu | Ala<br>315 | Ser | His | Leu | Asn | Leu<br>320 | Ala |
| Met | Cys | His | Leu | Lys<br>325 | Leu | Gln | Ala | Phe | Ser<br>330 | Ala | Ala | Ile | Glu | Ser<br>335 | Cys |
| Asn | Lys | Ala | Leu<br>340 | Glu | Leu | Asp | Ser | Asn<br>345 | Asn | Glu | Lys | Gly | Leu<br>350 | Phe | Arg |
| Arg | Gly | Glu<br>355 | Ala | His | Leu | Ala | Val<br>360 | Asn | Asp | Phe | Asp | Leu<br>365 | Ala | Arg | Ala |
| Asp | Phe<br>370 | Gln | Lys | Val | Leu | Gln<br>375 | Leu | Tyr | Pro | Ser | Asn<br>380 | Lys | Ala | Ala | Lys |
| Thr<br>385 | Gln | Leu | Ala | Val | Cys<br>390 | Gln | Gln | Arg | Thr | Arg<br>395 | Arg | Gln | Leu | Ala | Arg<br>400 |
| Glu | Lys | Lys | Leu | Tyr<br>405 | Ala | Asn | Met | Phe | Glu<br>410 | Arg | Leu | Ala | Glu<br>415 | Glu | Glu |
| His | Lys | Val | Lys<br>420 | Ala | Glu | Val | Ala | Ala<br>425 | Gly | Asp | His | Pro | Thr<br>430 | Asp | Ala |
| Glu | Arg | Lys<br>435 | Ser | Leu | Pro | Arg | Val<br>440 | Trp | Pro | Pro | Met | Asp<br>445 | Thr | Lys | Met |
| Gln | Ser<br>450 | Leu | Pro | Thr | Thr | His<br>455 | Pro | His | Pro | His | Ser<br>460 | Ser | Ser | Arg | Pro |
| Gln<br>465 | Ser | His | Thr | Ser | Asn<br>470 | Gln | Cys | Asn | Gln | Cys<br>475 | Thr | Cys | Ser | His | His<br>480 |
| Cys | Arg | Ser | Cys | Ser<br>485 | Gln | Ala | Gly | His | Ala<br>490 | Gly | Ser | Ser | Ser | Ser<br>495 | Pro |
| Ser | Pro | Gly | Pro<br>500 | Pro | Met | Lys | His | Pro<br>505 | Lys | Pro | Ser | Val | His<br>510 | Ser | Arg |
| His | Ser | Pro<br>515 | Ala | Arg | Pro | Ser | His<br>520 | Arg | Gly | Ser | Cys | Pro<br>525 | Lys | Asn | Arg |
| Lys | Thr<br>530 | Phe | Glu | Gly | Lys | Val<br>535 | Ser | Lys | Arg | Lys | Ala<br>540 | Val | Arg | Arg | Arg |
| Lys<br>545 | Arg | Thr | His | Arg | Ala<br>550 | Lys | Arg | Arg | Ser | Ser<br>555 | Gly | Arg | Arg | Tyr | Lys<br>560 |

( 2 ) INFORMATION FOR SEQ ID NO:23:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Ala<br>1 | Arg | Gly | Gly | Gly<br>5 | Glu | Arg | Gly | Ala | Val<br>10 | Gly | Val | Pro | Leu | Glu<br>15 | Gly |
| Val | Asp | Ile | Ser<br>20 | Pro | Lys | Gln | Asp | Glu<br>25 | Gly | Val | Leu | Lys | Val<br>30 | Ile | Lys |
| Arg | Glu | Gly<br>35 | Thr | Gly | Thr | Glu | Thr<br>40 | Pro | Met | Ile | Gly | Asp<br>45 | Arg | Val | Phe |
| Val | His<br>50 | Tyr | Thr | Gly | Trp | Leu<br>55 | Leu | Asp | Gly | Thr | Lys<br>60 | Phe | Asp | Ser | Ser |
| Leu<br>65 | Asp | Arg | Lys | Asp | Lys<br>70 | Phe | Ser | Phe | Asp | Leu<br>75 | Gly | Lys | Gly | Glu | Val<br>80 |
| Ile | Lys | Ala | Trp | Asp<br>85 | Ile | Ala | Val | Ala | Thr<br>90 | Met | Lys | Val | Gly | Glu<br>95 | Val |
| Cys | His | Ile | Thr | Cys | Lys | Pro | Glu | Tyr | Ala | Tyr | Gly | Ala | Ala | Gly | Ser |

|     |     |     |     |     | 100 |     |     |     |     | 105 |     |     |     |     | 110 |     |     |
|-----|-----|-----|-----|-----|-----|-----|-----|-----|-----|-----|-----|-----|-----|-----|-----|-----|-----|

Pro Pro Lys Ile Pro Pro Asn Ala Thr Leu Val Phe Glu Val Glu Leu
         115             120                 125

Phe Glu Phe Lys Gly Glu Asp Leu Thr Glu Glu Glu Asp Gly Gly Ile
130             135                 140

Ile Arg Arg Ile Arg Leu Gly Val Lys Ala Met Gln Gly Pro Asn Asp
145             150                 155                     160

Gly Ala Met Val Glu Val Ala Leu Glu Gly Tyr His Lys Asp Arg Leu
                165             170                 175

Phe Asp Gln Arg Glu Leu Cys Phe Glu Val Gly Glu Gly Glu Ser Leu
            180             185                 190

Asp Leu Pro Cys Ala Trp Arg Arg Pro Phe Ser Ala Trp Arg Lys Glu
        195             200                 205

Ser Ile Pro Ser Cys Thr Ser Asn Leu Ala Met Leu Leu Ala Val Trp
        210             215                 220

Gly Arg Arg Gly Ser Arg Ser His Arg Thr Ala Glu Leu Arg Tyr Glu
225             230                 235                     240

Val Arg Leu Lys Ser Phe Glu Lys Ala Lys Glu Ser Trp Glu Met Ser
            245             250                 255

Ser Ala Arg Ser Trp Ser Arg Ala Thr Tyr Val Lys Glu Arg Gly Thr
        260             265                 270

Ala Tyr Phe Lys Glu Gly Lys Tyr Lys Gln Ala Leu Leu Gln Tyr Lys
        275             280                 285

Lys Ile Val Ser Trp Leu Glu Tyr Glu Ser Ser Phe Ser Gly Glu Glu
    290             295                 300

Met Gln Lys Val His Ala Leu Arg Leu Ala Ser His Leu Asn Leu Ala
305             310                 315                     320

Met Cys His Leu Lys Leu Gln Ala Phe Ser Ala Ala Ile Glu Ser Cys
            325             330                 335

Asn Lys Ala Leu Glu Leu Asp Ser Asn Asn Glu Lys Gly Leu Phe Arg
            340             345                 350

Arg Gly Glu Ala His Leu Ala Val Asn Asp Phe Asp Leu Ala Arg Ala
        355             360                 365

Asp Phe Gln Lys Val Leu Gln Leu Tyr Pro Ser Asn Lys Ala Ala Lys
    370             375                 380

Thr Gln Leu Ala Val Cys Gln Gln Arg Thr Arg Arg Gln Leu Ala Arg
385             390                 395                     400

Glu Lys Lys Leu Tyr Ala Asn Met Phe Glu Arg Leu Ala Glu Glu Glu
            405             410                 415

His Lys Val Lys Ala Glu Val Ala Ala Gly Asp His Pro Thr Asp Ala
            420             425                 430

Glu Met Lys Gly Glu Arg Asn Asn Val Ala Glu Asn Gln Ser Arg Val
        435             440                 445

Glu Thr Glu Ala
450

( 2 ) INFORMATION FOR SEQ ID NO:24:

( i ) SEQUENCE CHARACTERISTICS:
        ( A ) LENGTH: 458 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

-continued

```
Met Thr Ala Glu Glu Met Lys Ala Ala Glu Ser Gly Ala Gln Ser Ala
 1           5                       10                      15

Pro Leu Pro Leu Glu Gly Val Asp Ile Ser Pro Lys Gln Asp Glu Gly
            20                  25              30

Val Leu Lys Val Ile Lys Arg Glu Gly Thr Gly Thr Glu Thr Pro Met
        35                  40              45

Ile Gly Asp Arg Val Phe Val His Tyr Thr Gly Trp Leu Leu Asp Gly
    50              55              60

Thr Lys Phe Asp Ser Ser Leu Asp Arg Lys Asp Lys Phe Ser Phe Asp
65                  70              75                      80

Leu Gly Lys Gly Glu Val Ile Lys Ala Trp Asp Ile Ala Val Ala Thr
                85                  90                  95

Met Lys Val Gly Glu Leu Cys Arg Ile Thr Cys Lys Pro Glu Tyr Ala
            100             105             110

Tyr Gly Ser Ala Gly Ser Pro Pro Lys Ile Pro Pro Asn Ala Thr Leu
            115             120             125

Val Phe Glu Val Glu Leu Phe Glu Phe Lys Gly Glu Asp Leu Thr Asp
    130             135             140

Asp Glu Asp Gly Gly Ile Ile Arg Arg Ile Arg Thr Arg Gly Glu Gly
145             150             155             160

Tyr Ala Arg Pro Asn Asp Gly Ala Ile Val Glu Val Ala Leu Glu Gly
                165             170             175

Tyr Tyr Lys Asp Arg Leu Phe Asp Gln Arg Glu Leu Arg Phe Glu Val
            180             185             190

Gly Glu Gly Glu Ser Leu Asp Leu Pro Cys Gly Leu Glu Lys Ala Ile
            195             200             205

Gln Arg Met Glu Lys Gly Glu His Ser Ile Leu Tyr Leu Lys Pro Ser
    210             215             220

Tyr Ala Phe Gly Asn Ala Gly Lys Glu Lys Phe Gln Ile Pro Pro Tyr
225             230             235             240

Ala Glu Leu Lys Tyr Glu Val His Leu Lys Ser Phe Glu Lys Ala Lys
            245             250             255

Glu Ser Trp Glu Met Ser Ser Glu Glu Lys Leu Glu Gln Ser Ala Ile
            260             265             270

Val Lys Glu Arg Gly Thr Val Tyr Phe Lys Glu Gly Lys Tyr Lys Gln
    275             280             285

Ala Leu Leu Gln Tyr Lys Lys Ile Val Ser Trp Leu Glu Tyr Glu Ser
290             295             300

Ser Phe Ser Ser Glu Glu Val Gln Lys Ala Gln Ala Leu Arg Leu Ala
305             310             315             320

Ser His Leu Asn Leu Ala Met Cys His Leu Lys Leu Gln Ala Phe Ser
            325             330             335

Ala Ala Val Glu Ser Cys Asn Lys Ala Leu Glu Leu Asp Ser Asn Asn
            340             345             350

Glu Lys Gly Leu Phe Arg Arg Gly Glu Ala His Leu Ala Val Asn Asp
            355             360             365

Phe Asp Leu Ala Arg Ala Asp Phe Gln Lys Val Leu Gln Leu Tyr Pro
    370             375             380

Ser Asn Lys Ala Ala Lys Ala Gln Leu Ala Val Cys Gln Gln Arg Ile
385             390             395             400

Arg Lys Gln Ile Ala Arg Glu Lys Lys Leu Tyr Ala Asn Met Phe Glu
            405             410             415

Arg Leu Ala Glu Glu Glu Asn Lys Ala Lys Ala Glu Val Ala Ala Gly
            420             425             430
```

```
          Asp His Pro Met Asp Thr Glu Met Lys Asp Glu Arg Asn Asp Val Ala
                      435                 440                 445

Gly Ser Gln Ser Gln Val Glu Thr Glu Ala
                      450                 455

( 2 ) INFORMATION FOR SEQ ID NO:25:

( i ) SEQUENCE CHARACTERISTICS:
              ( A ) LENGTH: 2157 base pairs
              ( B ) TYPE: nucleic acid
              ( C ) STRANDEDNESS: double
              ( D ) TOPOLOGY: linear ( i i ) MOLECULE TYPE: DNA (genomic)

( i x ) FEATURE:
              ( A ) NAME/KEY: CDS
              ( B ) LOCATION: 100..1476

( x i ) SEQUENCE DESCRIPTION: SEQ ID NO:25:

CCCGGCCTCC CGCACGCCCC GCAGGTAGCG CCCCCGCCCG CGGCCCAGAG TGCGCTCGCG              60

CCGGCACCAG CTCCCGGATA AACGGCGCGC CGCGCGGAG ATG ACA GCC GAG GAG              114
                                             Met Thr Ala Glu Glu
                                              1               5

ATG AAG GCG ACC GAG AGC GGG GCG CAG TCG GCG CCG CTG CCC ATG GAG              162
Met Lys Ala Thr Glu Ser Gly Ala Gln Ser Ala Pro Leu Pro Met Glu
         10                  15                  20

GGA GTG GAC ATC AGC CCC AAA CAG GAC GAA GGC GTG CTG AAG GTC ATC              210
Gly Val Asp Ile Ser Pro Lys Gln Asp Glu Gly Val Leu Lys Val Ile
             25                  30                  35

AAG AGA GAG GGC ACA GGT ACA GAG ATG CCC ATG ATT GGG GAC CGA GTC              258
Lys Arg Glu Gly Thr Gly Thr Glu Met Pro Met Ile Gly Asp Arg Val
     40                  45                  50

TTT GTC CAC TAC ACT GGC TGG CTA TTA GAT GGC ACA AAG TTT GAC TCC              306
Phe Val His Tyr Thr Gly Trp Leu Leu Asp Gly Thr Lys Phe Asp Ser
 55                  60                  65

AGT CTG GAT CGC AAG GAC AAA TTC TCC TTT GAC CTG GGA AAA GGG GAG              354
Ser Leu Asp Arg Lys Asp Lys Phe Ser Phe Asp Leu Gly Lys Gly Glu
 70                  75                  80                  85

GTC ATC AAG GCT TGG GAC ATT GCC ATA GCC ACC ATG AAG GTG GGG GAG              402
Val Ile Lys Ala Trp Asp Ile Ala Ile Ala Thr Met Lys Val Gly Glu
             90                  95                 100

GTG TGC CAC ATC ACC TGC AAA CCA GAA TAT GCC TAC GGT TCA GCA GGC              450
Val Cys His Ile Thr Cys Lys Pro Glu Tyr Ala Tyr Gly Ser Ala Gly
            105                 110                 115

AGT CCT CCA AAG ATT CCC CCC AAT GCC ACG CTT GTA TTT GAG GTG GAG              498
Ser Pro Pro Lys Ile Pro Pro Asn Ala Thr Leu Val Phe Glu Val Glu
        120                 125                 130

TTG TTT GAG TTT AAG GGA GAA GAT CTG ACG GAA GAG GAA GAT GGC GGA              546
Leu Phe Glu Phe Lys Gly Glu Asp Leu Thr Glu Glu Glu Asp Gly Gly
        135                 140                 145

ATC ATT CGC AGA ATA CAG ACT CGC GGT GAA GGC TAT GCT AAG CCC AAT              594
Ile Ile Arg Arg Ile Gln Thr Arg Gly Glu Gly Tyr Ala Lys Pro Asn
150                 155                 160                 165

GAG GGT GCT ATC GTG GAG GTT GCA CTG GAA GGG TAC TAC AAG GAC AAG              642
Glu Gly Ala Ile Val Glu Val Ala Leu Glu Gly Tyr Tyr Lys Asp Lys
                170                 175                 180

CTC TTT GAC CAG CGG GAG CTC CGC TTT GAG ATT GGC GAG GGG GAG AAC              690
Leu Phe Asp Gln Arg Glu Leu Arg Phe Glu Ile Gly Glu Gly Glu Asn
                    185                 190                 195

CTG GAT CTG CCT TAT GGT CTG GAG AGG GCC ATT CAG CGC ATG GAG AAA              738
Leu Asp Leu Pro Tyr Gly Leu Glu Arg Ala Ile Gln Arg Met Glu Lys
```

| | | | | | | | | | | | | | | | | |
|---|---|---|---|---|---|---|---|---|---|---|---|---|---|---|---|---|
| | | | | 200 | | | | | 205 | | | | | 210 | | |
| GGA | GAA | CAT | TCC | ATC | GTG | TAC | CTC | AAG | CCC | AGC | TAT | GCT | TTT | GGC | AGT | 786 |
| Gly | Glu | His | Ser | Ile | Val | Tyr | Leu | Lys | Pro | Ser | Tyr | Ala | Phe | Gly | Ser | |
| | 215 | | | | 220 | | | | | 225 | | | | | | |
| GTT | GGG | AAG | GAA | AAG | TTC | CAA | ATC | CCA | CCA | AAT | GCT | GAG | CTG | AAA | TAT | 834 |
| Val | Gly | Lys | Glu | Lys | Phe | Gln | Ile | Pro | Pro | Asn | Ala | Glu | Leu | Lys | Tyr | |
| 230 | | | | | 235 | | | | | 240 | | | | | 245 | |
| GAA | TTA | CAC | CTC | AAG | AGT | TTT | GAA | AAG | GCC | AAG | GAG | TCT | TGG | GAG | ATG | 882 |
| Glu | Leu | His | Leu | Lys | Ser | Phe | Glu | Lys | Ala | Lys | Glu | Ser | Trp | Glu | Met | |
| | | | | 250 | | | | | 255 | | | | | 260 | | |
| AAT | TCA | GAA | GAG | AAG | CTG | GAA | CAG | AGC | ACC | ATA | GTG | AAA | GAG | CGG | GGC | 930 |
| Asn | Ser | Glu | Glu | Lys | Leu | Glu | Gln | Ser | Thr | Ile | Val | Lys | Glu | Arg | Gly | |
| | | | 265 | | | | | 270 | | | | | 275 | | | |
| ACT | GTG | TAC | TTC | AAG | GAA | GGT | AAA | TAC | AAG | CAA | GCT | TTA | CTA | CAG | TAT | 978 |
| Thr | Val | Tyr | Phe | Lys | Glu | Gly | Lys | Tyr | Lys | Gln | Ala | Leu | Leu | Gln | Tyr | |
| | | 280 | | | | | 285 | | | | | 290 | | | | |
| AAG | AAG | ATC | GTG | TCT | TGG | CTG | GAA | TAT | GAG | TCT | AGT | TTT | TCC | AAT | GAG | 1026 |
| Lys | Lys | Ile | Val | Ser | Trp | Leu | Glu | Tyr | Glu | Ser | Ser | Phe | Ser | Asn | Glu | |
| | 295 | | | | | 300 | | | | | 305 | | | | | |
| GAA | GCA | CAG | AAA | GCA | CAG | GCC | CTT | CGA | CTG | GCC | TCT | CAC | CTC | AAC | CTG | 1074 |
| Glu | Ala | Gln | Lys | Ala | Gln | Ala | Leu | Arg | Leu | Ala | Ser | His | Leu | Asn | Leu | |
| 310 | | | | | 315 | | | | | 320 | | | | | 325 | |
| GCC | ATG | TGT | CAT | CTG | AAA | CTA | CAG | GCC | TTC | TCT | GCT | GCC | ATT | GAA | AGC | 1122 |
| Ala | Met | Cys | His | Leu | Lys | Leu | Gln | Ala | Phe | Ser | Ala | Ala | Ile | Glu | Ser | |
| | | | | 330 | | | | | 335 | | | | | 340 | | |
| TGT | AAC | AAG | GCC | CTA | GAA | CTG | GAC | AGC | AAC | AAC | GAG | AAG | GGC | CTC | TTC | 1170 |
| Cys | Asn | Lys | Ala | Leu | Glu | Leu | Asp | Ser | Asn | Asn | Glu | Lys | Gly | Leu | Phe | |
| | | | 345 | | | | | 350 | | | | | 355 | | | |
| CGC | CGG | GGA | GAG | GCC | CAC | CTG | GCC | GTG | AAT | GAC | TTT | GAA | CTG | GCA | CGG | 1218 |
| Arg | Arg | Gly | Glu | Ala | His | Leu | Ala | Val | Asn | Asp | Phe | Glu | Leu | Ala | Arg | |
| | | 360 | | | | | 365 | | | | | 370 | | | | |
| GCT | GAT | TTC | CAG | AAG | GTC | CTG | CAG | CTC | TAC | CCC | AAC | AAC | AAA | GCC | GCC | 1266 |
| Ala | Asp | Phe | Gln | Lys | Val | Leu | Gln | Leu | Tyr | Pro | Asn | Asn | Lys | Ala | Ala | |
| | 375 | | | | | 380 | | | | | 385 | | | | | |
| AAG | ACC | CAG | CTG | GCT | GTG | TGC | CAG | CAG | CGG | ATC | CGA | AGG | CAG | CTT | GCC | 1314 |
| Lys | Thr | Gln | Leu | Ala | Val | Cys | Gln | Gln | Arg | Ile | Arg | Arg | Gln | Leu | Ala | |
| 390 | | | | | 395 | | | | | 400 | | | | | 405 | |
| CGG | GAG | AAG | AAG | CTC | TAT | GCC | AAT | ATG | TTT | GAG | AGG | CTG | GCT | GAG | GAG | 1362 |
| Arg | Glu | Lys | Lys | Leu | Tyr | Ala | Asn | Met | Phe | Glu | Arg | Leu | Ala | Glu | Glu | |
| | | | | 410 | | | | | 415 | | | | | 420 | | |
| GAG | AAC | AAG | GCC | AAG | GCA | GAG | GCT | TCC | TCA | GGA | GAC | CAT | CCC | ACT | GAC | 1410 |
| Glu | Asn | Lys | Ala | Lys | Ala | Glu | Ala | Ser | Ser | Gly | Asp | His | Pro | Thr | Asp | |
| | | | 425 | | | | | 430 | | | | | 435 | | | |
| ACA | GAG | ATG | AAG | GAG | GAG | CAG | AAG | AGC | AAC | ACG | GCA | GGG | AGC | CAG | TCT | 1458 |
| Thr | Glu | Met | Lys | Glu | Glu | Gln | Lys | Ser | Asn | Thr | Ala | Gly | Ser | Gln | Ser | |
| | | 440 | | | | | 445 | | | | | 450 | | | | |
| CAG | GTG | GAG | ACA | GAA | GCA | TAGCCCCTCT | | CCACCAGCCC | | TACTCCTGCG | | | | | | 1506 |
| Gln | Val | Glu | Thr | Glu | Ala | | | | | | | | | | | |
| | 455 | | | | | | | | | | | | | | | |

| | | |
|---|---|---|
| GCTGCCTGCC CCCCAGTCTC CCCACTCCAC CCTGTTAGTT TTGTAAAAAC TGAAGAATTT | 1566 |
| TGAGTGAATT AGACCTTTAT TTTCTATCT GGTTGGATGG TGGCTTTAGG GGAAGGGGGA | 1626 |
| AAGGTGTAGG CTGGGGGATT GAGGTGGGGA ATCATTTTAG CTGGTGTCAG CCCCTCTTCC | 1686 |
| CTTCCTCCAT TGCACATGAA CATATGTCCA TCCATATATA TTCATCAGAA TGTTAATTTA | 1746 |
| TTTTGCTCCC TCTGTTAGGT CCATTTTCTA AGGGTAGAAG AGGCAAGTGG TAGGGATGAG | 1806 |
| GTCTGATAAG AACCCAGGGT GGAGAGGGAG ACTCCTGGGC AGCCGTTTTC CTCATCCTTT | 1866 |
| CCCTCTCCCA GTCCATTTCC AAATGTGGCC TCCATGTGGG TGCTAGGGAC ATGGGAAAAA | 1926 |

```
CCACTGCTAT  GCCATTTCTT  CTCTCTGTTC  CCTTCCTCAC  CCCCGACGGT  GTGGCTGATG    1986

ATGTCTTCTG  GTGTCATGGT  GACCACCCCC  TGTTCCCTGT  TCTGGTATTT  CCCCTGTCAG    2046

TTTCCCCTCT  CGGCCAGGTT  GTGTCCCAAA  ATCCCCTCAG  CCTCTTCTCT  GCACGTTGCT    2106

GAAGGTCCAG  GCTTGCCTCA  AGTTCCATGC  TTGAGCAATA  AAGTGGAAAC  A             2157
```

( 2 ) INFORMATION FOR SEQ ID NO:26:

( i ) SEQUENCE CHARACTERISTICS:
    ( A ) LENGTH: 459 amino acids
    ( B ) TYPE: amino acid
    ( D ) TOPOLOGY: linear ( i i ) MOLECULE TYPE: protein ( x i ) SEQUENCE DESCRIPTION: SEQ ID NO:26:

```
Met  Thr  Ala  Glu  Glu  Met  Lys  Ala  Thr  Glu  Ser  Gly  Ala  Gln  Ser  Ala
 1              5                        10                       15

Pro  Leu  Pro  Met  Glu  Gly  Val  Asp  Ile  Ser  Pro  Lys  Gln  Asp  Glu  Gly
               20                        25                       30

Val  Leu  Lys  Val  Ile  Lys  Arg  Glu  Gly  Thr  Gly  Thr  Glu  Met  Pro  Met
          35                        40                       45

Ile  Gly  Asp  Arg  Val  Phe  Val  His  Tyr  Thr  Gly  Trp  Leu  Leu  Asp  Gly
     50                        55                       60

Thr  Lys  Phe  Asp  Ser  Ser  Leu  Asp  Arg  Lys  Asp  Lys  Phe  Ser  Phe  Asp
65                       70                       75                       80

Leu  Gly  Lys  Gly  Glu  Val  Ile  Lys  Ala  Trp  Asp  Ile  Ala  Ile  Ala  Thr
                85                       90                       95

Met  Lys  Val  Gly  Glu  Val  Cys  His  Ile  Thr  Cys  Lys  Pro  Glu  Tyr  Ala
               100                       105                      110

Tyr  Gly  Ser  Ala  Gly  Ser  Pro  Pro  Lys  Ile  Pro  Pro  Asn  Ala  Thr  Leu
          115                       120                      125

Val  Phe  Glu  Val  Glu  Leu  Phe  Glu  Phe  Lys  Gly  Glu  Asp  Leu  Thr  Glu
     130                       135                      140

Glu  Glu  Asp  Gly  Gly  Ile  Ile  Arg  Arg  Ile  Gln  Thr  Arg  Gly  Glu  Gly
145                       150                      155                      160

Tyr  Ala  Lys  Pro  Asn  Glu  Gly  Ala  Ile  Val  Glu  Val  Ala  Leu  Glu  Gly
                165                       170                      175

Tyr  Tyr  Lys  Asp  Lys  Leu  Phe  Asp  Gln  Arg  Glu  Leu  Arg  Phe  Glu  Ile
               180                       185                      190

Gly  Glu  Gly  Glu  Asn  Leu  Asp  Leu  Pro  Tyr  Gly  Leu  Glu  Arg  Ala  Ile
          195                       200                      205

Gln  Arg  Met  Glu  Lys  Gly  Glu  His  Ser  Ile  Val  Tyr  Leu  Lys  Pro  Ser
     210                       215                      220

Tyr  Ala  Phe  Gly  Ser  Val  Gly  Lys  Glu  Lys  Phe  Gln  Ile  Pro  Pro  Asn
225                       230                      235                      240

Ala  Glu  Leu  Lys  Tyr  Glu  Leu  His  Leu  Lys  Ser  Phe  Glu  Lys  Ala  Lys
                245                       250                      255

Glu  Ser  Trp  Glu  Met  Asn  Ser  Glu  Glu  Lys  Leu  Glu  Gln  Ser  Thr  Ile
               260                       265                      270

Val  Lys  Glu  Arg  Gly  Thr  Val  Tyr  Phe  Lys  Glu  Gly  Lys  Tyr  Lys  Gln
          275                       280                      285

Ala  Leu  Leu  Gln  Tyr  Lys  Lys  Ile  Val  Ser  Trp  Leu  Glu  Tyr  Glu  Ser
     290                       295                      300

Ser  Phe  Ser  Asn  Glu  Glu  Ala  Gln  Lys  Ala  Gln  Ala  Leu  Arg  Leu  Ala
305                       310                      315                      320
```

```
Ser  His  Leu  Asn  Leu  Ala  Met  Cys  His  Leu  Lys  Leu  Gln  Ala  Phe  Ser
               325                      330                     335

Ala  Ala  Ile  Glu  Ser  Cys  Asn  Lys  Ala  Leu  Glu  Leu  Asp  Ser  Asn  Asn
               340                      345                     350

Glu  Lys  Gly  Leu  Phe  Arg  Arg  Gly  Glu  Ala  His  Leu  Ala  Val  Asn  Asp
               355                      360                     365

Phe  Glu  Leu  Ala  Arg  Ala  Asp  Phe  Gln  Lys  Val  Leu  Gln  Leu  Tyr  Pro
     370                      375                     380

Asn  Asn  Lys  Ala  Ala  Lys  Thr  Gln  Leu  Ala  Val  Cys  Gln  Gln  Arg  Ile
385                      390                     395                          400

Arg  Arg  Gln  Leu  Ala  Arg  Glu  Lys  Lys  Leu  Tyr  Ala  Asn  Met  Phe  Glu
               405                      410                     415

Arg  Leu  Ala  Glu  Glu  Asn  Lys  Ala  Lys  Ala  Glu  Ala  Ser  Ser  Gly
               420                      425                     430

Asp  His  Pro  Thr  Asp  Thr  Glu  Met  Lys  Glu  Glu  Gln  Lys  Ser  Asn  Thr
               435                      440                     445

Ala  Gly  Ser  Gln  Ser  Gln  Val  Glu  Thr  Glu  Ala
               450                 455
```

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CTCGAAGGAG TGGACATCAG C        21

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

ACTTTCCCCT TCCCCGACTT C        21

( 2 ) INFORMATION FOR SEQ ID NO:29:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

GCCACACTTG TATTTGAGGT G        21

( 2 ) INFORMATION FOR SEQ ID NO:30:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:30:

GCGGATCCAT CGAGGGTAGA ATGACAGCCG AGGAGATGA    39

(2) INFORMATION FOR SEQ ID NO:31:

(i) SEQUENCE CHARACTERISTICS:
 (A) LENGTH: 34 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:31:

CTCAGCTAAT TAAGCTTATG CTTCTGTCTC CACC    34

(2) INFORMATION FOR SEQ ID NO:32:

(i) SEQUENCE CHARACTERISTICS:
 (A) LENGTH: 102 amino acids
 (B) TYPE: amino acid
 (D) TOPOLOGY: linear (i i) MOLECULE TYPE: protein (x i) SEQUENCE DESCRIPTION: SEQ ID NO:32:

```
Gly Xaa Xaa Xaa Xaa Xaa Xaa Xaa Xaa Xaa Xaa Xaa Xaa Xaa Xaa Gly
 1               5                  10                  15
Xaa Xaa Xaa Xaa Xaa His Tyr Xaa Gly Xaa Leu Xaa Xaa Gly Xaa Xaa
             20                  25                  30
Phe Asp Xaa Ser Xaa Xaa Xaa Xaa Xaa Pro Xaa Xaa Xaa Xaa Xaa Gly
         35                  40                  45
Xaa Gln Val Ile Xaa Gly Trp Xaa Xaa Gly Xaa Xaa Xaa Xaa Xaa Xaa
     50                  55                  60
Gly Xaa Xaa Xaa Xaa Leu Xaa Ile Xaa Xaa Xaa Xaa Tyr Gly Xaa Xaa
 65                  70                  75                  80
Xaa Xaa Xaa Xaa Xaa Ile Pro Xaa Xaa Xaa Thr Leu Xaa Phe Xaa Xaa
             85                  90                  95
Glu Leu Xaa Lys Xaa Xaa
            100
```